(12) United States Patent
Johanek

(10) Patent No.: US 8,923,976 B2
(45) Date of Patent: Dec. 30, 2014

(54) MOVEMENT PATTERNS FOR ELECTRICAL STIMULATION THERAPY

(71) Applicant: Medtronic, Inc., Minneapolis, MN (US)

(72) Inventor: Lisa M. Johanek, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/750,381

(22) Filed: Jan. 25, 2013

(65) Prior Publication Data

US 2013/0289664 A1 Oct. 31, 2013

Related U.S. Application Data

(60) Provisional application No. 61/638,826, filed on Apr. 26, 2012.

(51) Int. Cl.
*A61N 1/36* (2006.01)

(52) U.S. Cl.
CPC ........ *A61N 1/36078* (2013.01); *A61N 1/36182* (2013.01); *A61N 1/36185* (2013.01); *A61N 1/3615* (2013.01)
USPC .......................................................... 607/46

(58) Field of Classification Search
CPC .............. A61N 1/36071; A61N 1/326; A61N 1/36021; A61N 1/025; A61N 1/0534; A61N 1/36146
USPC .................................................... 607/46–49
See application file for complete search history.

(56) References Cited

U.S. PATENT DOCUMENTS

| | | |
|---|---|---|
| 5,437,608 A | 8/1995 | Cutler |
| 7,117,034 B2 | 10/2006 | Kronberg |
| 7,167,752 B2 | 1/2007 | Lin-Hendel |
| 7,489,966 B2 | 2/2009 | Leinders et al. |
| 8,155,750 B2 | 4/2012 | Jaax et al. |
| 2006/0190057 A1* | 8/2006 | Reese ............................. 607/46 |
| 2007/0073356 A1 | 3/2007 | Rooney et al. |
| 2008/0208283 A1* | 8/2008 | Vetter et al. ..................... 607/45 |

* cited by examiner

*Primary Examiner* — Rex R Holmes
(74) *Attorney, Agent, or Firm* — Shumaker & Sieffert, P.A.

(57) ABSTRACT

Devices, systems, and techniques for delivering electrical stimulation according to a spatial electrode movement pattern are disclosed. Moving electrical stimulation between electrodes in a repeatable movement pattern may provide a therapeutic sensation to a patient. In one example, a system may include a plurality of electrodes configured to be implanted within a patient, at least one processor, and a therapy module. The at least one processor may be configured to receive a spatial electrode movement pattern that defines a sequence with which electrical stimulation is moved between the plurality of electrodes. The therapy module may be configured to deliver electrical stimulation to the patient based on the spatial electrode movement pattern. The therapy module may also be configured to move the electrical stimulation between each of the plurality of electrodes according to the spatial electrode movement pattern and repeat the spatial electrode movement pattern when delivering the electrical stimulation to the patient.

23 Claims, 12 Drawing Sheets

MOVEMENT PATTERNS FOR ELECTRICAL STIMULATION THERAPY

TECHNICAL FIELD

The disclosure relates to electrical stimulation therapy and, more particularly, changing parameter values for electrical stimulation therapy.

BACKGROUND

Electrical stimulators may be external or implanted, and may be used to deliver electrical stimulation therapy to patients to various nerve and/or tissue sites to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses, although other continuous waveforms may also be used. An implantable stimulator may deliver neurostimulation therapy via one or more leads that include electrodes located proximate to target locations associated with the brain, the spinal cord, pelvic nerves, peripheral nerves, or the gastrointestinal tract of a patient. Hence, stimulation may be used in different therapeutic applications, such as deep brain stimulation (DBS), spinal cord stimulation (SCS), pelvic stimulation, gastric stimulation, or peripheral nerve field stimulation (PNFS).

In general, a clinician may select values for a number of programmable parameters in order to define the electrical stimulation therapy to be delivered by the implantable stimulator to a patient. For example, the clinician ordinarily selects one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient. The clinician may create one or more programs that each includes a selected set of these stimulation parameters. As the patient receives therapy over time, the patient may select, or the system may automatically select, different programs to change the electrical stimulation. Each program may be directed to treat a different anatomical region of the patient, provide an alternative therapy, address a different symptom, or otherwise adjust the stimulation therapy.

SUMMARY

In general, the disclosure is directed to devices, systems, and techniques for delivering electrical stimulation according to a spatial electrode movement pattern. An implantable medical device (IMD) may generate electrical stimulation that is moved between a plurality of electrode groups or electrode combinations in a repeatable movement pattern. This movement of the electrical stimulation may elicit a wave of paresthesia or other sensation that moves through the patient to provide a therapeutic sensation to a patient. The electrical stimulation may have an intensity that allows the electrical stimulation to be perceived by the patient or even elicit motor function in the patient. In this manner, the electrical stimulation may provide moving paresthesia therapy, massaging type therapy, or even acupuncture type therapy. In some examples, this electrical stimulation movement maybe delivered in addition to another electrical stimulation therapy delivered by a subset of the plurality of electrodes.

In one example, the disclosure is directed to a method fir delivering electrical stimulation to a patient. The method includes receiving, by at least one processor, a spatial electrode movement pattern that defines a sequence with which electrical stimulation is moved between a plurality of electrodes implanted within the patient, delivering electrical stimulation to the patient based on the spatial electrode movement pattern, wherein the electrical stimulation is moved between each of the plurality of electrodes according to the spatial electrode movement pattern, and repeating the spatial electrode movement pattern when delivering the electrical stimulation to the patient.

In another example, the disclosure is directed to a system that includes plurality of electrodes configured to be implanted within a patient, at least one processor configured to receive a spatial electrode movement pattern that defines a sequence with which electrical stimulation is moved between the plurality of electrodes, and a therapy module configured to deliver electrical stimulation to the patient based on the spatial electrode movement pattern, wherein the at least one processor is configured to control the therapy module to move the electrical stimulation between each of the plurality of electrodes according to the spatial electrode movement pattern and control the therapy module to repeat the spatial electrode movement pattern when delivering the electrical stimulation to the patient.

In a further example, the disclosure is directed to a computer-readable storage medium comprising instructions that cause at least one processor to receive a spatial electrode movement pattern that defines a sequence with which electrical stimulation is moved between plurality of electrodes implanted within a patient, deliver electrical stimulation to the patient based on the spatial electrode movement pattern, wherein the electrical stimulation is moved between each of the plurality of electrodes according to the spatial electrode movement pattern, and repeat the spatial electrode movement pattern when delivering the electrical stimulation to the patient.

The details of one or more example are set forth in the accompanying drawings and the description below. Other features, objects, and advantages will be apparent from the description and drawings, and from the claims.

DETAILED DESCRIPTION

Figure 1:
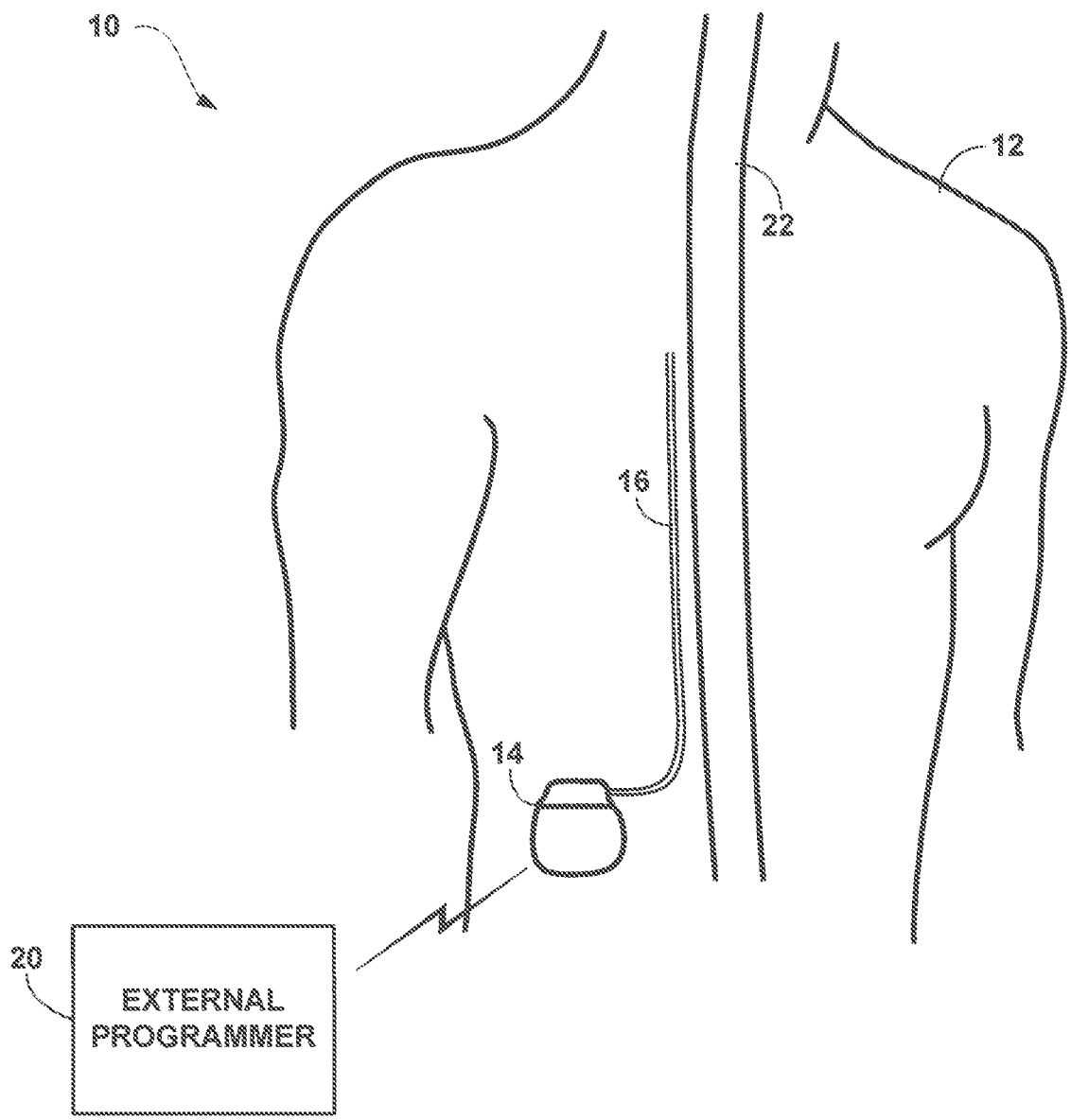
FIG. 1 is a conceptual diagram illustrating an example system that includes an implantable medical device (IMD) for delivering spinal cord stimulation therapy.

This disclosure is generally directed to devices, systems, and techniques for delivering electrical stimulation according to a spatial electrode movement pattern. Electrical stimulation therapy may be delivered to a patient to treat one or more symptoms (e.g., chronic pain or physiological dysfunction). The electrical stimulation may be defined by a set of stimulation parameters (e.g., a program) such as current or voltage amplitude, pulse rate or frequency, pulse width, and electrode combination. Different programs or different stimulation parameters may be used such that electrical stimulation affects different areas of the patient over time. However, changes may be made in an attempt to find one or more sets of stimulation parameters that define electrical stimulation that is effective for treating the patient.

As disclosed herein, an implantable medical device (IMD) or other therapy device may be configured such that electrical stimulation is purposefully moved between a plurality of electrodes, such as between a plurality of electrode groups, to provide therapy. The electrodes used to deliver stimulation may be arranged at different spatial positions over time. Accordingly, this movement (e.g., a repeatable spatial electrode movement pattern) may cause different tissues or nerve fibers to be affected by the electrical stimulation and change the sensation perceived by the patient. This changing sensation from the moving electrical stimulation may be perceived as a massaging therapy, acupuncture therapy, or even a migrating paresthesia. For example, the movement in the electrical stimulation may be perceived by the patient as a wave of an intense feeling or larger area of paresthesia. This movement or wave may, in some examples, make higher intensity and more efficacious stimulation more tolerable to the patient. The type of sensation may also be affected by other stimulation parameters such as the current or voltage amplitude, pulse width, pulse frequency, and unipolar or bipolar electrode combinations.

In some examples, the electrical stimulation delivered according to the spatial electrode movement pattern may be delivered above a perception threshold. The perception threshold may be representative of a stimulation intensity defined by an amplitude, a pulse frequency, a pulse width, or some combination thereof, above which the patient is capable of perceiving the electrical stimulation. Stimulation intensities near the perception threshold may provide paresthesia (e.g., an acceptable sensation that replaces pain or other undesirable feelings) that migrate with the spatial electrode movement pattern. Simulation intensities further above the perception threshold may elicit stronger paresthesia or acupuncture-like therapy to the areas of the patient affected by the stimulation. Alternatively, or additionally, the electrical stimulation may be delivered at an intensity above a therapeutic threshold (e.g., above an intensity that provides a therapeutic benefit to the patient). In some examples, the electrical stimulation may be delivered below a pain threshold (e.g., a threshold at which the stimulation is perceived by the patient has painful or uncomfortable). However, in other examples, the electrical stimulation may be delivered above a pain threshold for each particular electrode combination in the pattern when the perceived pain is tolerable due to the movement of the stimulation between a plurality of electrode combinations.

In other examples, the electrical stimulation delivered according to the spatial electrode movement patterns may be delivered above a motor threshold. The motor threshold may be representative of a stimulation intensity defined by an amplitude, a pulse frequency, a pulse width, or some combination thereof, above which muscle fibers contract. Stimulation intensities above the motor threshold may elicit a massaging effect on the patient as stimulation is moved according to the spatial electrode movement pattern.

The spatial electrode movement pattern may define a sequence with which electrode stimulation moves between a plurality of electrodes. The sequence may be repeatable and configured in a particular shape. For example, the shape of the spatial electrode movement pattern may be circular, rectangular, or some other form. Although the spatial electrode movement pattern may follow adjacent electrodes, the movement pattern may traverse between non-adjacent electrodes in some examples. In other examples, the spatial electrode movement pattern may be randomly generated. The plurality of electrodes may include four or more electrodes, all of the electrodes implanted within a patient, or a subset of the electrodes implanted within a patient.

The electrical stimulation may be provided separately such that only electrodes selected by the spatial electrode movement pattern at a given time are active (e.g., a cathode or anode). In other examples, the electrical stimulation may be delivered concurrently (e.g., at the same time or interleaved) with background stimulation. For example, the electrical stimulation being moved according to the spatial electrode movement pattern may be selected with a high intensity to elicit a massaging or acupuncture type sensation. The high intensity stimulation may activate A-delta fibers that simulate an acupuncture-like feeling. The background stimulation delivered by other electrodes may be selected with a low intensity to elicit general paresthesia when the high intensity stimulation is not being delivered to that anatomical area of the patient. In other words, each electrode of a plurality of electrodes may deliver electrical stimulation with the high intensity or the low intensity. In some examples, the background stimulation and the high intensity stimulation may be delivered by the same electrodes on an alternating pulse basis. This alternating pulse basis may be referred to as interleaving pulses or interleaving two or more different electrode stimulation therapies.

As described herein, moving electrical stimulation between a plurality of electrodes may be used to treat temporary or chronic pain of the patient. The electrical stimulation may be delivered via peripheral nerve field stimulation (PNFS) leads or spinal cord stimulation (SCS) leads in some examples. Moving electrical stimulation may provide unique therapy to address varying pain symptoms, allow for therapeutic high intensity stimulation during a relatively brief period of time, and/or reduce the likelihood of accommodation to any stationary stimulation therapy (i.e., therapy that is delivered via a fixed set of electrodes rather than moved among different electrodes).

FIG. 1 is a conceptual diagram illustrating example system 10 that includes an implantable medical device (IMD) 14 for delivering spinal cord stimulation (SCS) therapy. Although the techniques described in this disclosure are generally disclosed with respect to pain management therapy for illustration, other types of therapy may incorporate one or more ramping techniques disclosed herein. In addition, FIG. 1 is directed to SCS therapy. However, system 10 may alternatively be configured to provide peripheral nerve field stimulation (PNFS) of FIG. 2, occipital nerve stimulation, sacral nerve stimulation (SNS), pelvic floor stimulation, or any other electrical stimulation therapy.

As shown in FIG. 1, system 10 includes an IMD 14 and external programmer 20 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally IMD 14 may be a chronic electrical stimulator that remains implanted within patient 12 for weeks, months, or even years. In the example of FIG. 1, IMD 14 and lead 16 may be directed to delivering SCS therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 may be coupled to one or more lead 16.

Electrical stimulation energy, which may be constant current or constant voltage based pulses, for example, is delivered from IMD 14 to one or more targeted locations within patient 12 via one or more electrodes (not shown) of lead 16. The parameters for a program that controls delivery of stimulation energy by IMD 14 may include information identifying which electrodes have been selected for delivery of stimulation according to a stimulation program, the combination of the selected electrodes, and the polarities of the selected electrodes, i.e., the electrode configuration for the program, and voltage or current amplitude, pulse frequency (or pulse rate), pulse shape, and pulse width of stimulation delivered by the electrodes. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 22 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector (not shown) that electrically couples to a header of IMD 14. Although only one lead 16 is shown in FIG. 1, system 10 may include two or more leads, each coupled to IMD 14 and directed to similar or different target tissue sites. For example, multiple leads may be disposed along spinal cord 22 or leads may be directed to spinal cord 22 and/or other locations within patient 12.

Lead 16 may carry one or more electrodes that are placed adjacent to the target tissue, e.g., spinal cord 22 for spinal cord stimulation (SCS) therapy. One or more electrodes may be disposed at or near a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. In general, ring electrodes arranged at different axial positions at the distal ends of lead 16 will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve field stimulation (PNFS), gastrointestinal stimulation, or other deep tissue or superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 22 (e.g., one or more target locations of the dorsal columns or one or more dorsal roots that branch from spinal cord 22). Lead 16 may be introduced into spinal cord 22 via any suitable region, such as the thoracic, cervical or lumbar regions. Stimulation of dorsal columns, dorsal roots, and/or peripheral nerves (e.g., afferent nerves) may, for example, prevent pain signals from traveling through spinal cord 22 and to the brain of the patient. Patient 12 may perceive the interruption of pain signals as a reduction in pain and, therefore, efficacious therapy results. For treatment of other disorders, lead 16 may be introduced at any exterior location of patient 12.

Although lead 16 is described as generally delivering or transmitting electrical stimulation signals, lead 16 may additionally transmit electrical signals from patient 12 to IMD 14 for monitoring. For example, IMD 14 may utilize detected nerve impulses to diagnose the condition of patient 12 or adjust the delivered stimulation therapy. Lead 16 may thus transmit electrical signals to and from patient 12.

A user, such as a clinician or patient 12, may interact with a user interface of an external programmer 20 to program IMD 14. Programming of IMD 14 may refer generally to the generation and transfer of commands, programs, or other information to control the operation of IMD 14. In this manner, IMD 14 may receive the transferred commands and programs from programmer 20 to control stimulation therapy. For example, external programmer 20 may transmit programs, parameter adjustments, program selections, group selections, user input, or other information to control the operation of IMD 14, e.g., by wireless telemetry or wired connection.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to hold a ramping amplitude or terminate or change stimulation therapy when the stimulation is undesirable. In general, a physician or clinician programmer may support selection and generation of programs by a clinician for use by stimulator 14, whereas a patient programmer may support adjustment and selection of such programs by a patient during ordinary use. In other examples, external programmer 20 may be included, or part of, an external charging device that recharges a power source of IMD 14. In this manner, a user may program and charge IMD 14 using one device, or multiple devices.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 14 may be configured to provide a hermetic seal thr components, such as rechargeable power source 18. In addition, the housing of IMD 14 may be selected of a material that facilitates receiving energy to charge rechargeable power source 18.

As described herein, information may be transmitted between external programmer 20 and IMD 14. Therefore, IMD 14 and programmer 20 may communicate via wireless communication using any techniques known in the art. Examples of communication techniques may include, for example, radiofrequency (RF) telemetry and inductive coupling, but other techniques are also contemplated. In some examples, programmer 20 may include a communication head that may be placed proximate to the patient's body near the IMD 14 implant site in order to improve the quality or security of communication between IMD 14 and programmer 20. Communication between programmer 20 and IMD 14 may occur during power transmission or separate from power transmission.

As further described herein, IMD 14 and/or programmer 20 may move electrical stimulation delivery between electrodes of lead 16 according to a spatial electrode movement pattern to achieve a desired therapeutic effect for patient 12. In one example, a system may include a plurality of electrodes configured to be implanted within a patient. The system may also include one or more processors (of IMD 14 and/or programmer 20) that may be configured to receive a spatial electrode movement pattern that defines a sequence with which electrical stimulation is moved between the plurality of electrodes. In addition, the system may include a therapy module configured to deliver electrical stimulation to the patient based on the spatial electrode movement pattern. Under control of one or more processors, the therapy module may also move the electrical stimulation between each of the plurality of electrodes according to the spatial electrode movement pattern, and repeat the spatial electrode movement pattern when delivering the electrical stimulation to the patient.

IMD 14 may house or otherwise include the therapy module configured to generate and deliver electrical stimulation to patient 12 when moving the electrode stimulation (e.g., changing electrode combinations). The therapy module may include an electrical stimulation generator and any circuits necessary to generate electrical stimulation pulses or waveforms according to the parameter values of the stimulation parameter set. Accordingly, the therapy module may generate stimulation pulses according to the stimulation parameters selected by one or more processors. The generated stimulation may be delivered via lead 16 to patient 12. IMD 14 and/or programmer 20 may house or otherwise include the at least one processor and the memory.

The one or more processors may receive or retrieve the spatial electrode movement pattern from a memory of IMD 14 or programmer 20 in some examples. The spatial electrode movement pattern may include the spatial sequence for electrode combination movement and/or timing for such movement. The memory may be configured to store one or more spatial electrode movement patterns. In other examples, the one or more processors may receive the spatial electrode movement pattern from a user interface of external programmer 20, wherein a user (e.g., patient 12 or a clinician) has provided input defining or selecting the spatial electrode movement pattern. In some examples, the user may select a spatial electrode movement pattern from a plurality of patterns presented on the user interface or modify a previously stored spatial electrode movement pattern.

The electrical stimulation delivered by the therapy module may be based on one or more spatial electrode movement patterns. As described herein, the spatial electrode movement pattern may define how the stimulation moves between a plurality of electrodes. In other words, the spatial electrode movement pattern may identify a sequence of electrode combinations or instruct the therapy module how to identify the next electrode combination to be used for delivering the electrical stimulation. In this manner, moving electrical stimulation may refer to changing electrode combinations such that the electrical field produced by the active electrodes moves with respect to patient anatomy to affect different anatomical regions of patient 12.

In addition, the electrical stimulation may be defined by a set of stimulation parameters. A single set of stimulation parameters may be referred to as a stimulation program. The set of stimulation parameters may include current or voltage amplitude, pulse width, pulse rate (or pulse frequency). In some examples, the set of stimulation parameters may also include an electrode combination that defines the starting electrodes to be used when initializing the spatial electrode movement pattern. In other examples, the set of stimulation parameters may include the spatial electrode movement pattern. Instead of the set of stimulation parameters including a single electrode combination, the set may include a sequence of multiple electrode combinations as the spatial electrode movement pattern. In this manner, a set of stimulation parameters may either be associated with a spatial electrode movement pattern or include the electrode movement patters as a parameter within the set. Alternatively, the spatial electrode movement pattern may be a group of programs, where each program defines a specific electrode combination or step) in the sequence of the spatial electrode movement pattern.

When delivering electrical stimulation to patient 12, IMD 14 may repeat the spatial electrode movement pattern. Electrical stimulation therapy may be delivered on a moving basis for minutes, hours, days, or even weeks at a time. During this time, the spatial electrode movement pattern may be repeated until IMD 14, the clinician, or patient 12 commands stimulation therapy to terminate. In some cases, electrode stimulation may be terminated in the middle of a spatial electrode movement pattern (e.g., prior to the entire sequence completing). When restarting electrical stimulation with the same spatial electrode movement pattern, IMD 14 may begin delivering electrical stimulation at the position in the spatial electrode movement pattern when stimulation was previously terminated or the starting position defined by the spatial electrode movement pattern.

The movement of the electrical stimulation may be defined by a position component and a temporal component. The sequence of electrode combination changes may be the position component because the sequence defines the position at which electrical stimulation will be delivered to patient 12. The temporal component may define the speed at which electrode combinations are changed according to the sequence. This temporal component may be referred to as the progression rate.

The progression rate may indicate the frequency at which electrode combinations in the sequence are changed. The progression rate may generally be between 0.01 Hz and 10 Hz. Hence, with this progression rate, a different electrode combination may be selected every 0.1 to 100 seconds. In one example, the progression rate may be between approximately 0.1 Hz and 5 Hz. In another example, the progression rate may be between approximately 0.2 Hz and 2 Hz. In specific examples, the progression rate may be approximately 1 Hz or approximately 2 Hz. Alternatively, the progression rate may indicate the period of time during which each electrode combination of the sequence is used to deliver the electrical stimulation, i.e., the period between changes in electrode combination. The progression rate may generally be between 0.1 seconds and 60 seconds. In one example, the progression rate may be between approximately 0.5 seconds and 5 seconds. In some examples, the spatial electrode movement pattern (or progression rate) may define movement of the electrical stimulation between at least two of electrodes at least once every 10 seconds. In other examples, progression rates may be lower or higher than the example rates provided herein.

Generally, the progression rate may be constant throughout the entire spatial electrode movement pattern. In other words, each electrode combination of the spatial electrode movement pattern may be used to deliver electrical stimulation for approximately equal durations of time. Alternatively, the progression rate may change during the spatial electrode movement pattern in other examples. For example, the progression rate may slow for electrode combinations at anatomical sites in need of longer duration of therapy. In other examples, the progression rate may slow for sensitive areas in which the stimulation intensity is ramped up over a longer duration of time.

During the spatial electrode movement pattern, electrical stimulation may be delivered as a series of pulses or burst of pulses. For example, the pulses delivered by one electrode combination of the spatial electrode movement pattern may be referred to as a burst of pulses. In this manner, the electrical stimulation may be delivered as a burst of pulses at one electrode combination and subsequently another burst of pulses at a second electrode combination of the spatial electrode movement pattern.

In some examples, the electrical stimulation may be delivered as a continuous series of pulses during the spatial electrode movement pattern. Each of these pulses may be defined by the same set of stimulation parameters. However, the electrode combination used to deliver these pulses may change according to the spatial electrode movement pattern. In other examples, the current or voltage amplitude may be ramped up when a new electrode combination is used to deliver the pulses. In this manner, each burst of pulses provided by an electrode combination may ramp up in stimulation intensity (e.g., current or voltage amplitude, pulse frequency, and/or pulse width) at the beginning of the burst. This ramping of stimulation intensity may be more acceptable by patient 12 and/or contribute to the massaging effect of stimulation when such massaging therapy is desired.

The spatial electrode movement pattern may take a variety of forms depending upon the desired therapy for a patient. In some examples, the spatial electrode movement pattern may include a circular or rectangular pattern among the plurality of electrodes. In other words, the spatial electrode movement pattern may rotate through adjacent the electrodes to move the electrical stimulation, in other examples, the spatial electrode movement pattern may take on other forms depending on where electrodes are implanted, whether or not the sequence changes between adjacent electrodes or skips physically adjacent electrodes in the sequence. In one example, the spatial electrode movement pattern may include a random pattern among the plurality of electrodes. The random pattern may include patterns that skip or move between electrodes in a nonlinear, non-circular, or otherwise unordered sequence. The random pattern may be originally generated randomly amongst the available electrodes and then repeated during the therapy.

In general, a spatial electrode movement pattern may utilize each of the plurality of electrodes once during the sequence of the pattern. In this manner, electrical stimulation may be moved through a greater area of patient 12. In other examples, a spatial electrode movement pattern may utilize one or more of the plurality of electrodes multiple times within the spatial electrode movement pattern. Electrodes used multiple times within spatial electrode movement pattern may allow electrical stimulation to target some anatomical regions more frequently than if all electrodes were used an equal amount of time.

In some examples, the spatial electrode movement pattern may define electrical stimulation movement among at least four electrodes. In other examples, the spatial electrode movement pattern may define electrical stimulation movement among at least eight electrodes or at least sixteen electrodes. Generally, the spatial electrode movement pattern may apply to any number of electrodes. The number of electrodes used to move the electrical stimulation may be equal to the total number of electrodes implanted within patient 12. However, in some examples, not all electrodes implanted within patient 12 may be used by the spatial electrode movement pattern to move the electrical stimulation within patient. In other words, the spatial electrode movement pattern may define stimulation movement using each of a subset of implanted electrodes or each electrode carried by one or more leads implanted within patient 12. Each electrode combination of the spatial electrode movement pattern may be mutually exclusive (e.g., each electrode is only used for only one electrode combination in one iteration of the spatial electrode movement pattern). Alternatively, multiple electrode combinations of the spatial electrode movement pattern may include one or more of the same electrodes.

The plurality of electrodes used to deliver the electrical stimulation may be carried by a single lead (e.g., lead 16). In other examples, the plurality of electrodes may be carried by two or more leads. The spatial electrode movement pattern may define movement between electrodes regardless of which lead the electrodes are on. In other words, the spatial electrode movement pattern may be determined based on the physical location of each electrode within patient 12, not which lead carries each electrode. Generally, a single IMD 14 may be coupled to the one or more leads for delivering electrical stimulation. In other examples, multiple implantable devices may be coupled to two or more leads and coordinated to deliver electrical stimulation according to one or more spatial electrode movement patterns.

The electrical stimulation moved according to the spatial electrode movement pattern may be the only stimulation delivered by the electrodes during the movement. This primary stimulation, however, may be delivered concurrently with a secondary stimulation. The primary stimulation may have a high intensity and the secondary stimulation may have a low intensity. The secondary stimulation may thus be described as a background stimulation that is provided to patient 12 by electrodes not delivering the primary stimulation. Alternatively, the secondary stimulation may also be delivered by the same electrodes of the high intensity stimulation on an alternating pulse or other alternating time pattern. In some examples, the background stimulation may be provided to deliver general paresthesia to patient 12 while the primary stimulation provides massaging or acupuncture type therapy to patient 12.

In this manner, IMD 14 may be configured to deliver primary electrical stimulation with high stimulation intensity to patient 12 via a first subset of a plurality of electrodes. At the same time, IMD 14 may be configured to deliver the secondary electrical stimulation with low stimulation intensity to the patient via a second subset of the plurality of electrodes different than the first subset. In other words, at any given time, the same electrode may not provide both the primary and secondary stimulation. Alternatively, the same electrode may be an anode for two or more different sets of cathodes, where one set of cathodes delivers the high intensity stimulation and another set of cathodes delivers the low intensity stimulation. The first and second subset of electrodes may include all of the plurality of electrodes in some examples. In addition, the high stimulation intensity may be greater than the low stimulation intensity. The low stimulation intensity of the secondary stimulation may be above a perception threshold and/or a therapeutic threshold. The high stimulation intensity may also be above the perception and therapeutic thresholds and may additionally be above a motor threshold in some examples.

In some examples, the therapy module of IMD 14 may be configured to deliver electrical stimulation that exceeds a perception threshold and/or a motor threshold. The electrical stimulation that exceeds the perception threshold may be configured to be perceived by patient 12. The perception threshold may be defined through tissue modeling or experimental data obtained by slowly ramping up amplitude or other stimulation parameters until patient 12 can feel the stimulation. The electrical stimulation that exceeds the motor threshold may be configured to cause muscle contractions in patient 12. For example, the electrical stimulation may have an amplitude, pulse rate, and/or pulse width sufficient to cause muscle contractions. The motor threshold may be defined through tissue modeling or experimental data obtained by slowly ramping up amplitude or other stimulation parameters until patient 12 can feel or observe muscle activity or a sensor detects the muscle activity. Similarly, IMD 14 may be configured to deliver electrical stimulation that exceeds a therapeutic threshold. The therapeutic threshold may be defined using experimental data obtained by slowly ramping up amplitude or other stimulation parameters until patient 12 can identify a therapeutic effect on one or more symptoms.

In some examples, the perception threshold, the motor threshold, and/or the therapeutic threshold may be related to each other. For example, as stimulation intensity is increased, the perception threshold may be exceeded, followed by the therapeutic threshold, and then followed by the motor threshold. However, these thresholds may be exceeded under relatively different intensities. For example, the motor threshold may be exceeded at a lower intensity than the perception threshold. In another example, the therapeutic threshold may be exceeded at a lower intensity than the perception threshold. The intensity level required to reach and exceed each of these thresholds may be specific to patient 12 and anatomical locations within patient 12.

In some examples, IMD 14 may be configured to deliver electrical stimulation via a plurality of unipolar electrode combinations defined by the spatial electrode movement pattern. Unipolar stimulation generally refers to a lead electrode being configured as a cathode or anode and a relatively distant electrode on the housing of IMD 14 as the opposing anode or cathode. In unipolar stimulation, all of the electrodes on lead 16, for example, may generally be configured as only cathodes or only anodes. In this manner, a spatial electrode movement pattern may define that each of the plurality of unipolar electrode combinations includes one or more of the electrodes and a housing electrode of IMD 14.

In other examples, IMD 14 may be configured to deliver electrical stimulation via a plurality of bipolar electrode combinations or multipolar electrode combinations defined by the spatial electrode movement pattern. Bipolar electrode stimulation generally refers to different electrodes of a lead being configured as one cathode and one anode, respectively. Multipolar electrode stimulation generally refers to different electrodes of a lead being configured as at least one cathode and at least one anode. Where bipolar electrode combinations are described herein, multipolar electrode combinations may alternatively be used. Each of the plurality of electrode combinations of the spatial electrode movement pattern may then include two or more of the electrodes of lead 16. Bipolar or multipolar electrical stimulation may be capable of delivering more focus and/or intense stimulation to patient 12 because the electrical field between relatively close anodes and cathodes is smaller and more focused than the electrical field from unipolar stimulation.

Although electrical stimulation movement between electrodes is generally described herein, massaging or acupuncture type stimulation therapy may be provided to patient 12 by delivering pulses on all or some of the electrodes at once. For example, IMD 14 may deliver bursts of one or more pulses to patient 12 using all electrodes of lead 16 at the same time. Delivery of electrical stimulation by all electrodes of one or more lead may be in the form of one or more pulses (e.g., a burst of pulses) a relatively short period of time. For example, the burst of pulses may be provided over a duration between approximately 0.1 seconds and 10 seconds. However, shorter or longer durations of the burst of pulses is also contemplated. In addition, this stimulation may be provided at higher intensities, such as above perception threshold, above therapeutic threshold, above motor threshold, and/or above pain threshold. This delivery of stimulation via all or many of the electrodes may be used with unipolar, bipolar, or multipolar stimulation techniques.

Although IMD 14 is generally described herein, techniques of this disclosure may also be applicable to external or partially external medical device in other examples. For example, IMD 14 may instead be configured as an external medical device coupled to one or more percutaneous medical leads. The external medical device may be a chronic, temporary, or trial electrical stimulator. In addition, an external electrical stimulator may be used in addition to one or more IMDs 14 to deliver electrical stimulation described herein.

Figure 2:
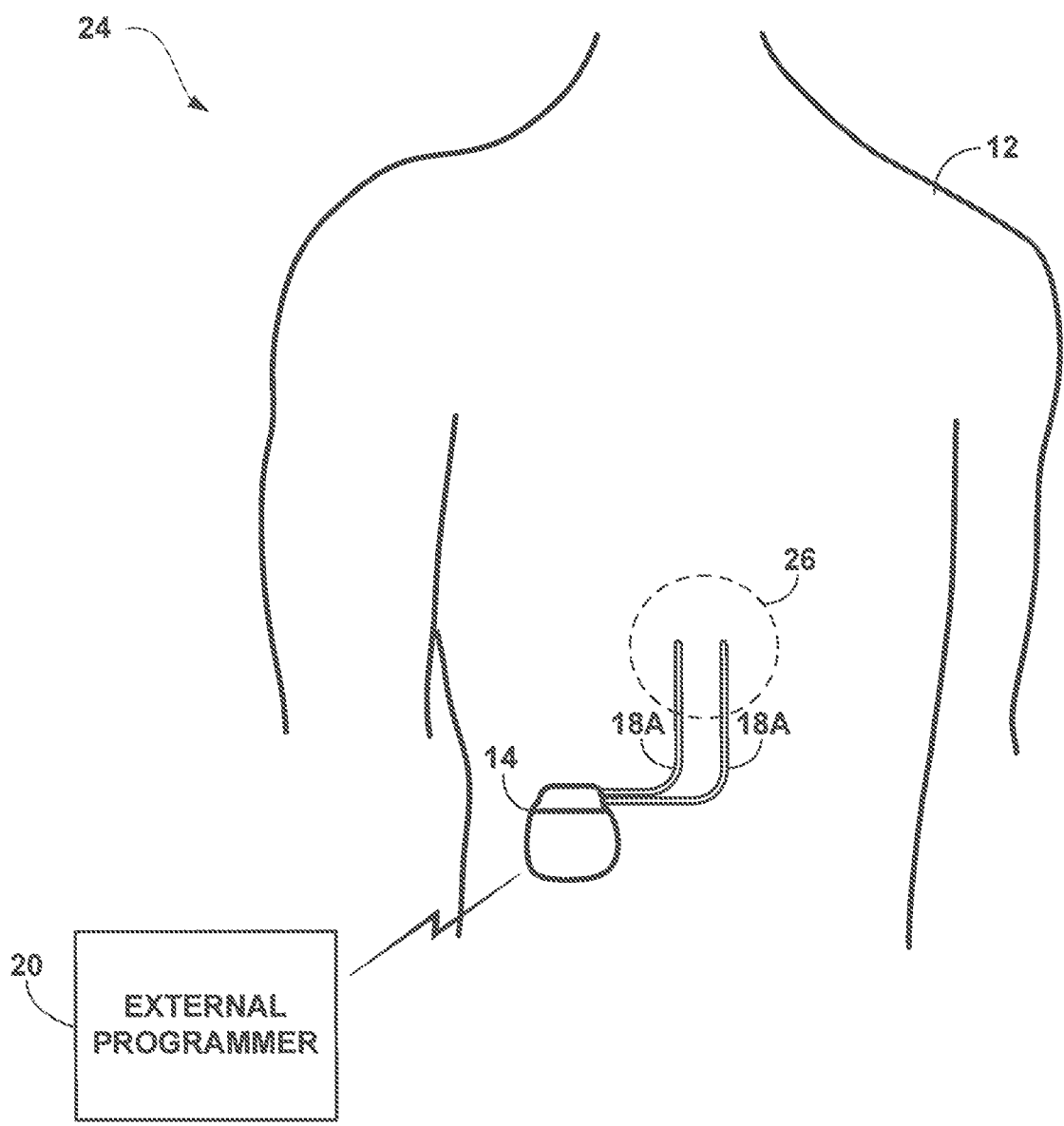
FIG. 2 is a conceptual diagram illustrating an example system that includes an implantable medical device (IMD) for delivering peripheral nerve stimulation therapy.

FIG. 2 is a conceptual diagram illustrating an example system 24 that includes IMD 14 for delivering peripheral nerve field stimulation (PNFS) therapy. IMD 14 may be configured to deliver PNFS therapy using any of the spatial electrode movement patterns or stimulation therapy described herein. PNFS may be delivered by a medical device via electrodes implanted in the region (e.g., region 26) where the patient experiences pain. Some examples of programming techniques described herein allow a user, such as a clinician or patient, to determine a therapy program for the PNFS based on user input that specifies one or more characteristics of the stimulation field that is delivered to the region in which the patient experiences pain. The characteristics of the stimulation field may include, fir example, a direction of stimulation within the field, a breadth of the stimulation field, a focus of stimulation within the stimulation field, a fiber diameter selectivity, and a depth of the stimulation field relative to a reference point, such as the epidermis of the patient.

As described with respect to FIG. 1, adjusting the stimulation intensity (e.g., adjusting amplitude (current or voltage) or pulse width) may modify the area 26 of which patient 12 perceives paresthesia or is subject to motor activation during delivery of electrical stimulation. A stimulation parameter set may be selected such that electrical stimulation reduces or eliminates the pain perceived by patient 12 within region 26. As electrical stimulation is moved according to the spatial electrode movement pattern, region 26 may move within patient 12. Although the center of region 26 may generally correlate with the electrode or electrodes activated at that particular time in the sequence of the spatial electrode movement pattern, various anatomical or physiological characteristics may change the shape and position of region 26 with respect to the active electrodes.

The stimulation parameter set may include an electrode combination using one or more electrodes of one or both leads 18A and 18B. Each of leads 18A and 18B may be similar to lead 16 of FIG. 1. Electrode combinations used to provide PNFS therapy may be unipolar (e.g., one or more cathodes are provided by lead 18A or 18B and an anode is provided on the housing of IMD 14) or bipolar (e.g., both cathodes and anodes are provided on leads 18A and/or 18B). In other examples, IMD 14 may be coupled to a single lead or more than two leads. Similar to FIG. 1, external programmer 20 may communicate with and transmit parameter sets or other commands to IMD 14. As described herein, the electrode combinations may be changed according to the spatial electrode movement pattern selected for therapy.

Some example systems may include more than one IMD 14 for delivery of PNFS to one or more regions in which patient 12 experiences pain. In other examples, may be delivered alone, or in combination with other therapies, such as spinal cord stimulation (SCS), deep brain stimulation (DBS), cortical stimulation (CS), drug therapy, and the like, as described in U.S. Patent Publication No. 2007/0073356 to Rooney et al., entitled, "COMBINATION THERAPY INCLUDING PERIPHERAL NERVE FIELD STIMULATION," which was filed on Jun. 9, 2006, and is incorporated herein by reference in its entirety.

In the example shown in FIG. 2, leads 18A and 18B deliver PNFS to the tissue of patient 12 within a region 26 where patient 12 experiences pain. Leads 18A and/or 18B may be implanted within or between, for example, intra-dermal, deep dermal, or subcutaneous tissues of patient 12 at the region 26 where patient 12 experiences pain to deliver PNFS. These tissue locations of leads 18A and 18B are generally subcutaneous and also external of the thoracic cavity or other internal organs. In other words, leads configured to deliver PNFS may be generally implanted within tissues associated within the skin of patient 12 or external of other non-skin tissues. Therefore, these tissues for PNFS implantation may include skin and associated nerves and muscles and associated nerves or muscle fibers. In the illustrated example, region 26 is an axial region of the lower back of patient 12, but the invention is not limited as such. Rather, leads 18A and 18B may be implanted in any region where patient 12 experiences pain. Leads 18A and/or 18B may deliver PNFS to one layer of tissue or multiple layers of a tissue as determined necessary by a clinician.

PNFS may ameliorate pain within the region of implantation by stimulating axons or small nerve fibers in the nearby dermal, subcutaneous, or muscular tissues, or the tissues themselves. The stimulation of these axons or fibers may cause orthodromic action potentials that propagate toward a spinal cord of patient 12, and modulate larger peripheral nerves (e.g., afferent nerves) and dorsal horn cells and/or synapses within the dermatomes that include the pain region, which may reduce pain experienced by patient 12 in that region. The stimulation of these axons or fibers may also cause antidromic action potentials that propagate toward the skin and modulate sympathetic outflow, which may reduce pain mediated by the sympathetic system, such as with some forms of complex regional pain syndrome. PNFS may also activate muscle fibers when the stimulation intensity exceeds the motor threshold.

Lead 18A or 18B may comprise, as examples, a substantially cylindrical lead with ring electrodes, a paddle lead, or a lead with a more complex, three-dimensional electrode array geometry, such as a cylindrical lead with electrodes disposed at various circumferential positions around the cylinder (e.g., with the aid of partial ring electrodes or segmented electrodes disposed at various circumferential positions around a lead having a generally round cross-section). In some examples, leads 18A or 18B may include electrodes, such as pad electrodes or segmented electrodes, on more than one surface. For example, leads 18A and 18B may be a paddle-type lead with electrodes on multiple surfaces, or a multiple level lead, as will be described in greater detail below. In general, the disclosure may be used with a system 10 including any type of lead, and is not limited to the leads described herein, or any particular type of implantable lead.

Figure 3:
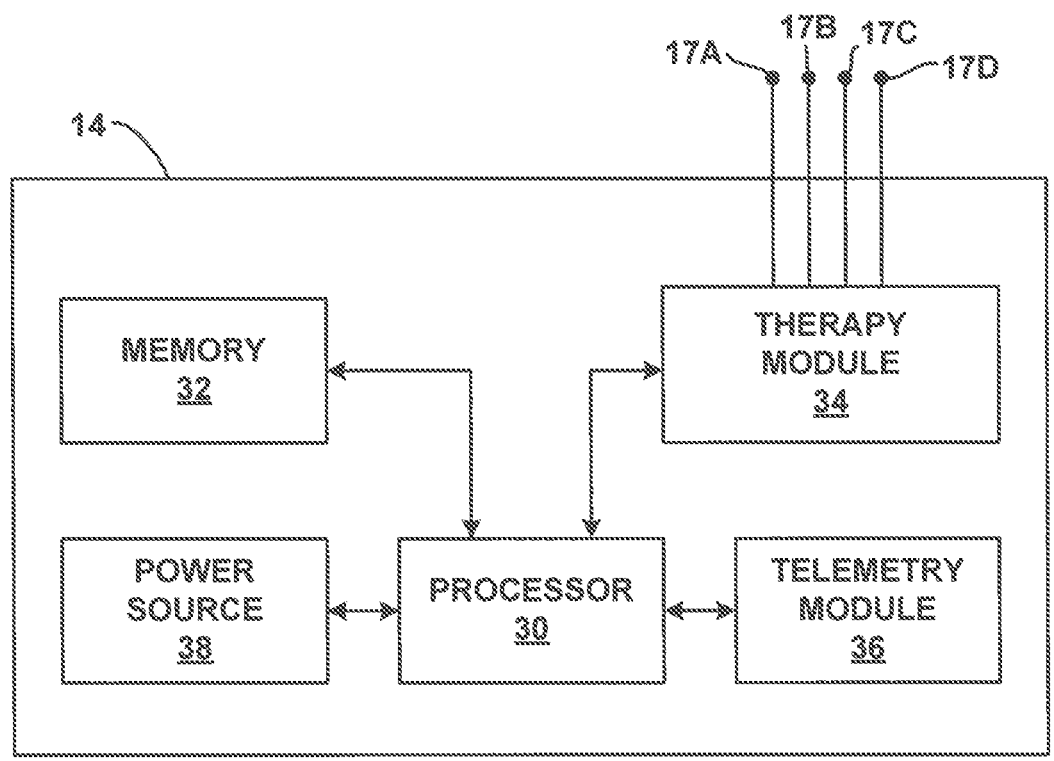
FIG. 3 is a block diagram of the example IMD of FIGS. 1 and 2.

FIG. 3 is a block diagram of the example IMD 14 of FIGS. 1 and 2. In the example of FIG. 3, IMD 14 includes processor 30, therapy module 34, power source 38, memory 32, and telemetry module 36. In other examples, IMD 14 may include a greater or fewer number of components. For example, IMD 14 may also include a temperature sensor, an inductive coil to receive power from an external charging device, and a recharge module that manages recharging of power source 38.

In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 30, therapy module 34, and telemetry module 36 are described as separate modules, in some examples, processor 30, therapy module 34, and telemetry module 36 may be functionally integrated. In some examples, processor 30, therapy module 34, and telemetry module 36 may correspond to individual hardware units, such as ASICs, DSPs, FPGAs, or other hardware units.

Memory 32 may store therapy programs or other instructions that specify therapy parameter values for the therapy provided by therapy module 34 and IMD 14. Memory 32 may also store spatial electrode movement patterns, perception, motor, and/or motor thresholds, one or more sets of stimulation parameters, and any other instructions tier moving electrical stimulation. Spatial electrode movement patterns may be stored to include a sequence or order of electrode combinations, a rate at which each electrode combination in the pattern is to be changed, or timing instructions that indicate when each electrode combination in the pattern is to be moved, in some examples, memory 32 may also store instructions for communication between IMD 14 and programmer 20, or any other instructions required to perform tasks attributed to IMD 14. Memory 32 may store a duplicate of the data stored in memory 52 of programmer 20.

Generally, therapy module 34 may generate and deliver electrical stimulation under the control of processor 30. In some examples, processor 30 controls therapy module 34 by accessing memory 32 to selectively access and load at least one of the stimulation programs to therapy module 34. For example, in operation, processor 30 may access memory 32 to load one of the stimulation programs to therapy module 34. In such examples, relevant stimulation parameters may include a voltage amplitude, a current amplitude, a pulse frequency, a pulse width, a duty cycle, one or more spatial electrode movement patterns that define the combination of electrodes 17A, 17B, 17C, and 17D that therapy module 34 uses to deliver the electrical stimulation signal. Although therapy module 34 may be configured to generate and deliver electrical stimulation therapy via one or more of electrodes 17A, 17B, 17C, and 17D of lead 16, a different therapy module may be configured to provide different therapy to patient 12, such as drug delivery therapy via a catheter. These and other therapies may be provided by IMD 14.

An exemplary range of electrical stimulation parameters that may be used to deliver effective treatment for chronic pain, e.g., when applied to spinal cord 18, are listed below. While stimulation pulses are described, stimulation signals may be of any of a variety of forms such as sine waves or the like.

Pulse Frequency: between approximately 0.5 Hz and 10,000 Hz. In one example, pulse frequency may be between approximately 5 Hz and 250 Hz or between approximately 30 Hz and 130 Hz. In other examples, pulse frequency may be greater than 250 Hz or even greater than 1,000 Hz. Pulse frequencies greater than 1,000 Hz may be considered to be greater than the nerve firing potential of affected nerve fibers to inhibit nerve firing. For example, the pulse frequency may be between approximately 1,000 Hz and 10,000 Hz.

Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between approximately 0.1 milliamps (mA) and 50 mA. In other examples, current amplitude may be between approximately 1.0 mA and 10 mA.

Pulse Width: between about 10 microseconds and 5000 microseconds. In some examples, the pulse width may be between approximately 100 microseconds and 1000 microseconds or between approximately 180 microseconds and 450 microseconds. With higher frequency pulses, the pulse width may be smaller to accommodate the increased frequency. For example, the pulse width may be between approximately 10 microseconds and 50 microseconds.

Memory 32 may store a plurality of spatial electrode movement patterns that define a sequence with which electrical stimulation is moved between implanted electrodes 17, for example. The spatial electrode movement patterns may be stored in a look-up table or other database. The look-up table may include a sequence of entries in which each identifies which electrodes of each electrode combination in the pattern are anodes and cathodes and/or the time at which stimulation is to be moved between each electrode combination. In some examples, spatial electrode movement patterns may be stored as a part of sets of stimulation parameters.

Processor 30 may select the appropriate spatial electrode movement pattern based on the requested therapy received from input entered to programmer 20. For example, programmer 20 may receive an input from a user (e.g., patient 12) that requests delivery of a massaging therapy or acupuncture type therapy. The user may also input the type of spatial electrode movement pattern desired, an intensity level for the therapy, and/or one or more parameters that at least partially define the intensity level. In another example, processor 30 may select the appropriate spatial electrode movement pattern based on a commanded therapy for patient 12 (e.g., a therapy determined based on stored therapy instructions or detected changes to a physiological parameter). Spatial electrode movement patterns may be stored as a predefined sequence of electrode combinations and/or one or more equations that are used to define the progression through the sequence of electrode combinations. In addition, the progression rate may be stored by memory 32 separately from the spatial electrode movement patterns or as a part of the respective spatial electrode movement patterns.

IMD 14 also includes components to receive power from programmer 20 or a separate charging device to recharge a batter of power source 38. Power source 38 may include one or more capacitors, batteries, or other energy storage devices. IMD 14 may thus also include an inductive coil and a recharge module (both not shown) configured to manage the recharging session for power source 38. Although inductive coupling may be used to recharge power source 38, other wireless energy transfer techniques may alternatively be used. Alternatively, power source 38 may not be rechargeable.

Processor 30 may also control the exchange of information with programmer 20 and/or an external programmer using telemetry module 36. Telemetry module 36 may be configured for wireless communication using radio frequency protocols or inductive communication protocols. Telemetry module 36 may include one or more antennas configured to communicate with programmer 20, for example. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36. For example, telemetry module 36 may receive user input, spatial electrode movement patterns, or other commands from programmer 20.

Figure 4:
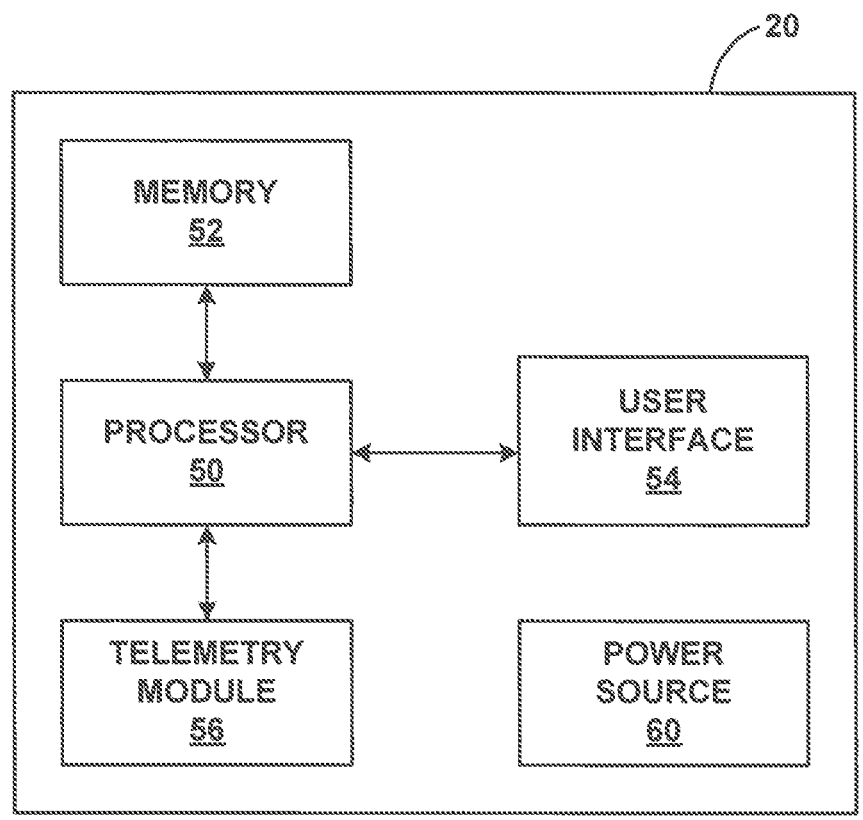
FIG. 4 is a block diagram of the example external programmer of FIGS. 1 and 2.

FIG. 4 is a block diagram of the example external programmer 20. While programmer 20 may generally be described as a hand-held device, programmer 20 may be a larger portable device or a more stationary device. In addition, in other examples, programmer 20 may be included as part of an external charging device or include the functionality of an external charging device. As illustrated in FIG. 4, programmer 20 may include a processor 50, memory 52, user interface 54, telemetry module 56, and power source 60. Memory 52 may store instructions that, when executed by processor 50, cause processor 50 and external programmer 20 to provide the functionality ascribed to external programmer 20 throughout this disclosure. For example, processor 50 may be configured to select a ramp schedule for increasing or decreasing a parameter value during delivery of electrical stimulation.

In general, programmer 20 comprises any suitable arrangement of hardware, alone or in combination with software and/or firmware, to perform the techniques attributed to programmer 20, and processor 50, user interface 54, and telemetry module 56 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 correspond to individual hardware units, such as ASICs, DSPs, FPGAs, or other hardware units.

Memory 52 may store instructions that, when executed by processor 50, cause processor 50 and programmer 20 to provide the functionality ascribed to programmer 20 throughout this disclosure. For example memory 52 may include instructions that cause processor 50 to obtain a parameter set from memory, select a spatial electrode movement pattern, or receive a user input and send a corresponding command to IMD 14, or instructions for any other functionality. In addition, memory 52 may include a plurality of programs, where each program includes a parameter set that defines stimulation therapy, and/or a plurality of spatial electrode movement patterns. In some examples, programmer 30 may select a spatial electrode movement pattern when a user provides input to start stimulation. In other examples, IMD 14 may request that programmer 30 selects a spatial electrode movement pattern and transmit the spatial electrode movement pattern, or at least one aspect of the spatial electrode movement pattern, back to IMD 14 for delivery and movement of the corresponding electrical stimulation.

User interface 54 may include a button or keypad, lights, a speaker for voice commands, a display, such as a liquid crystal (LCD), light-emitting diode (LED), or organic light-emitting diode (OLED). In some examples the display may be a touch screen. User interface 54 may be configured to display any information related to the delivery of stimulation therapy, such as currently selected parameter values, spatial electrode movement patterns, progression rates, intensity thresholds, or any other therapy information. User interface 54 may also receive user input via user interface 54. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

In some examples, user interface 54 may receive an input from patient 12 or another user that requests the type of therapy to be delivered by IMD 14. For example, user interface 54 may receive a request a massage therapy, acupuncture therapy, standard pain therapy, or any other therapy described herein. In addition, user interface 54 may receive selections specific to a type of therapy. For example, the user may select a spatial electrode movement pattern from one or more listed patterns or create a new spatial electrode movement pattern. The user may also select the progression rate at which each electrode configuration of the pattern is changed or parameters values that at least partially define the intensity of stimulation. In some examples, the user may input a request for an abstract level of the identified type of therapy. For example, the user may select from "low," "medium," or "high" intensity levels for the therapy. Processor 50 and/or processor 30 may then determine the appropriate stimulation parameters, or even the spatial electrode movement pattern, based on the abstract selection.

In some examples, user interface 54 may display the status or progress of the stimulation movement as it is being delivered to patient 12. For example, user interface 54 may display the implanted leads and/or electrodes and highlight or otherwise mark the electrodes being used to deliver stimulation at any given time. In other examples, user interface 54 may display a more abstract illustration of current therapy. For example, user interface 54 may display the general spatial electrode movement pattern in conjunction with a lead or in conjunction with an anatomical region of patient 12 (e.g., an illustration of the patient's back). Alternatively, user interface 54 may illustrate the intended anatomical region with a moving area (e.g., a circle or amorphous shape) that represents the location of currently delivered electrical stimulation. In addition, or alternatively, to presenting the current status of the stimulation movement in these graphical illustrations, the clinician or patient 12 may similarly program the spatial electrode movement patterns with graphical methods (e.g., an anatomical region or leads with the desired areas to be affected during the movement of stimulation).

Telemetry module 56 may support wireless communication between IMD 14 and programmer 20 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna.

Examples of local wireless communication techniques that may be employed to facilitate communication between programmer 20 and IMD 14 include RF communication according to the 802.11 or Bluetooth specification sets or other standard or proprietary telemetry protocols. In this manner, other external devices may be capable of communicating with programmer 20 without needing to establish a secure wireless connection. As described herein, telemetry module 56 may be configured to transmit a spatial electrode movement pattern or other stimulation parameter values to IMD 14 for delivery of stimulation therapy.

Figure 5:
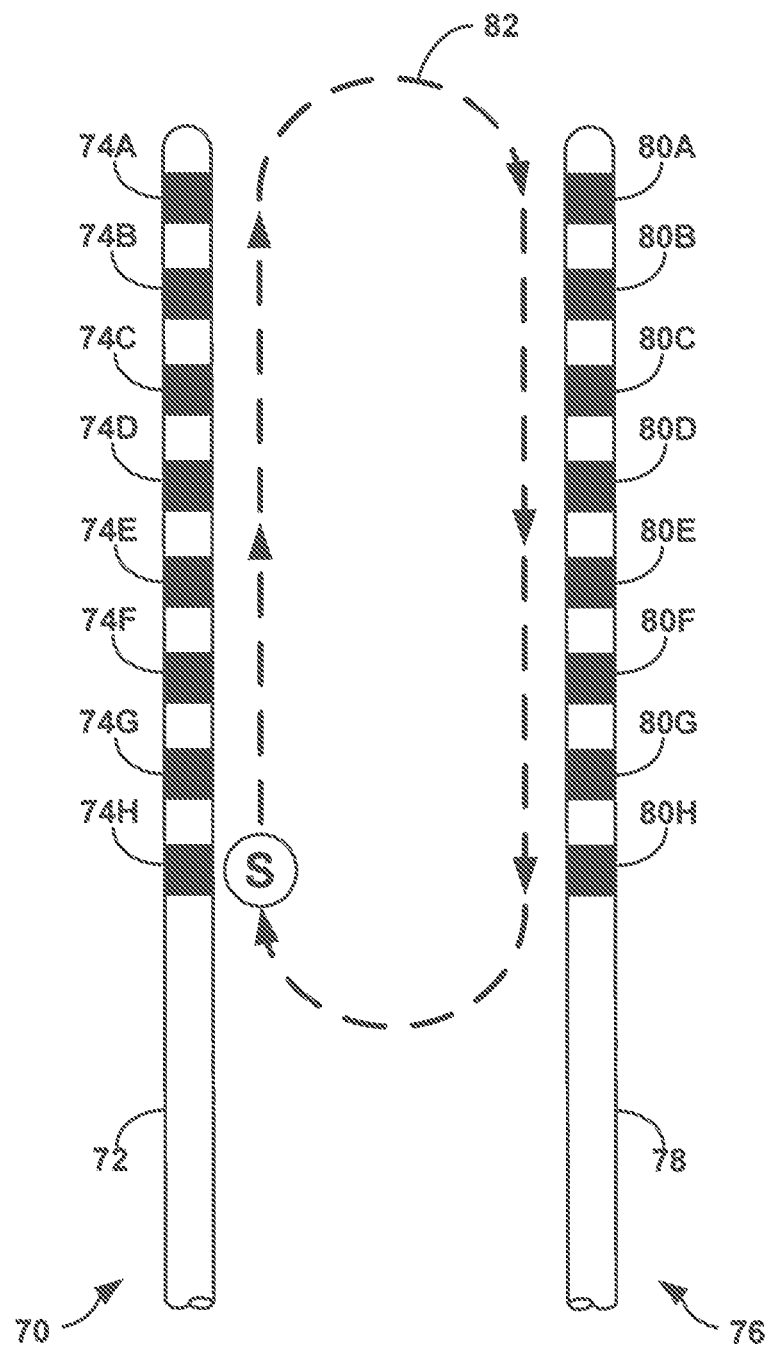
FIG. 5 is a conceptual diagram illustrating an example circular spatial electrode movement pattern for moving electrical stimulation between a plurality of electrodes.

FIG. 5 is a conceptual diagram illustrating an example circular spatial electrode movement pattern 82 for moving electrical stimulation between a plurality of electrodes using unipolar electrode combinations. As shown in FIG. 5, leads 70 and 76 may be configured to be implanted within patient 12 and coupled to IMD 14. Leads 70 and 76 may be similar to leads 16, 18A, and/or 18B. Lead 70 may include lead body 72 that carries eight electrodes 74A, 74B, 74C, 74D, 74E, 74F, 74G, and 74H (collectively "electrodes 74"). Lead 76 may include lead body 78 that carries eight electrodes 80A, 80B, 80C, 80D, 80E, 80F, 80G, and 80H (collectively "electrodes 80").

When electrode stimulation is selected to be delivered by electrodes 74 and 80, spatial electrode movement pattern 82 may be selected to define the sequence with which active electrodes are moved between electrodes 74 and 80. For example, IMD 14 may start delivering electrical stimulation at electrode 74H (at least part of an electrode combination) as indicated by the "S" icon. Each selected electrode in spatial electrode movement pattern 82 may be a cathode, for examples. The electrode on the housing of IMD 14 may be the associated anode for each electrode combination of the spatial electrode movement pattern. In other examples, one of electrodes 74 or 80 may be the stationary anode and the cathode may be moved amongst the remainder of electrodes 74 and 80 (or a subset of electrodes 74 and 80).

When the progression rate indicates that stimulation is to be moved, IMD 14 may terminate stimulation with electrode 74H and then subsequently begin stimulation with electrode 74G according to the sequence of spatial electrode movement pattern 82. Movement of the active electrode may continue in the direction of the arrows of spatial electrode movement pattern 82 (e.g., up lead 70 and then down lead 76) until instructions command the stimulation is changed or stopped or a user provides an input to terminate the stimulation. Spatial electrode movement pattern 82 may also repeat until stimulation is terminated.

In a unipolar stimulation configuration as shown in FIG. 5, only one electrode of leads 70 and 76 may be used for each electrode combination of spatial electrode movement pattern 82. For example, an electrode of leads 70 and 76 may be a cathode and the electrode carried on the housing of IMD 14 may be an anode, or vice versa. Although only one electrode 74 and 80 is shown as active at any given time (e.g., a cathode) during spatial electrode movement pattern 82, multiple electrodes 74 and/or 80 may be used as cathodes for each electrode combination of the sequence in spatial electrode movement pattern 82 to deliver stimulation. The multiple electrodes may be adjacent electrodes, electrodes separated by one or more electrodes, or even electrodes on both leads 70 and 76. In other examples, multiple electrodes 74 and/or 80 may be used in a bipolar or multipolar configuration and moved in the circular manner of spatial electrode movement pattern 82.

Each time that electrical stimulation is moved to a new electrode combination (e.g., electrode 74H to electrode 74G), IMD 14 may ramp up the amplitude of the electrical stimulation. This ramp up of amplitude may be performed to reduce abrupt sensations to patient 12. This ramp up of amplitude or another stimulation parameter may be completed within 10 seconds, for example. In some examples, the ramp may be completed within one or more pulses of the burst provided by the electrode combination.

Although stimulation may be started at electrode 74H, stimulation may be started at any position within spatial electrode movement pattern 82. For example, stimulation may be started at electrode 74D or electrode 80E. The starting position may be selected by patient 12, the clinician, or based on the last electrode used during a previous time the stimulation was provided to patient 12.

Spatial electrode movement pattern 82 is provided in a clockwise direction around electrodes 74 and 80. In other examples, spatial electrode movement pattern 82 may move in a counterclockwise direction. The direction of spatial electrode movement pattern 82 may be selected by the clinician, selected by patient 12, or alternated between repetitions of spatial electrode movement pattern 82 or instances that therapy is delivered using spatial electrode movement pattern 82. Spatial electrode movement pattern 82 may generally be described as a circular or rectangular pattern. In other examples, spatial electrode movement pattern 82 may represent patterns of other forms or shapes. For examples, the spatial electrode movement pattern may define a sequence of electrode combinations that move back and forth between leads 70 and 76. In addition, alternative spatial electrode movement patterns 82 may include random sequences for moving the electrical stimulation.

Leads 70 and 76 may include an equal number of electrodes. In other examples, leads 70 and 76 may include unequal numbers of electrodes. In some examples, more than two leads may be used or only one lead may be used. In the example of a single lead (e.g., only lead 70), the spatial electrode movement pattern may define traversal of all electrodes 74 from one end of lead 70 to the opposite end of lead 70 and back again. Alternatively, the spatial electrode movement pattern may only move in one direction such that the electrode movement pattern restarts at one end of lead 70 when the sequence finishes at the opposite end of lead 70.

Movement of electrical stimulation may be performed using all of the electrodes of implanted leads 70 and 76, for example. However, fewer than all of the electrodes may be utilized for a spatial electrode movement pattern in other examples. Generally, four or more electrodes may be utilized when moving electrical stimulation. For example, eight electrodes, sixteen electrodes, or even thirty two or more electrodes may be utilized. However, fewer than four electrodes may be used in some examples. In other examples, the clinician or patient 12 may blacklist or remove one or more electrodes from a spatial electrode movement pattern if that electrode provides an uncomfortable or otherwise undesirable sensation to patient 12.

Figure 6:
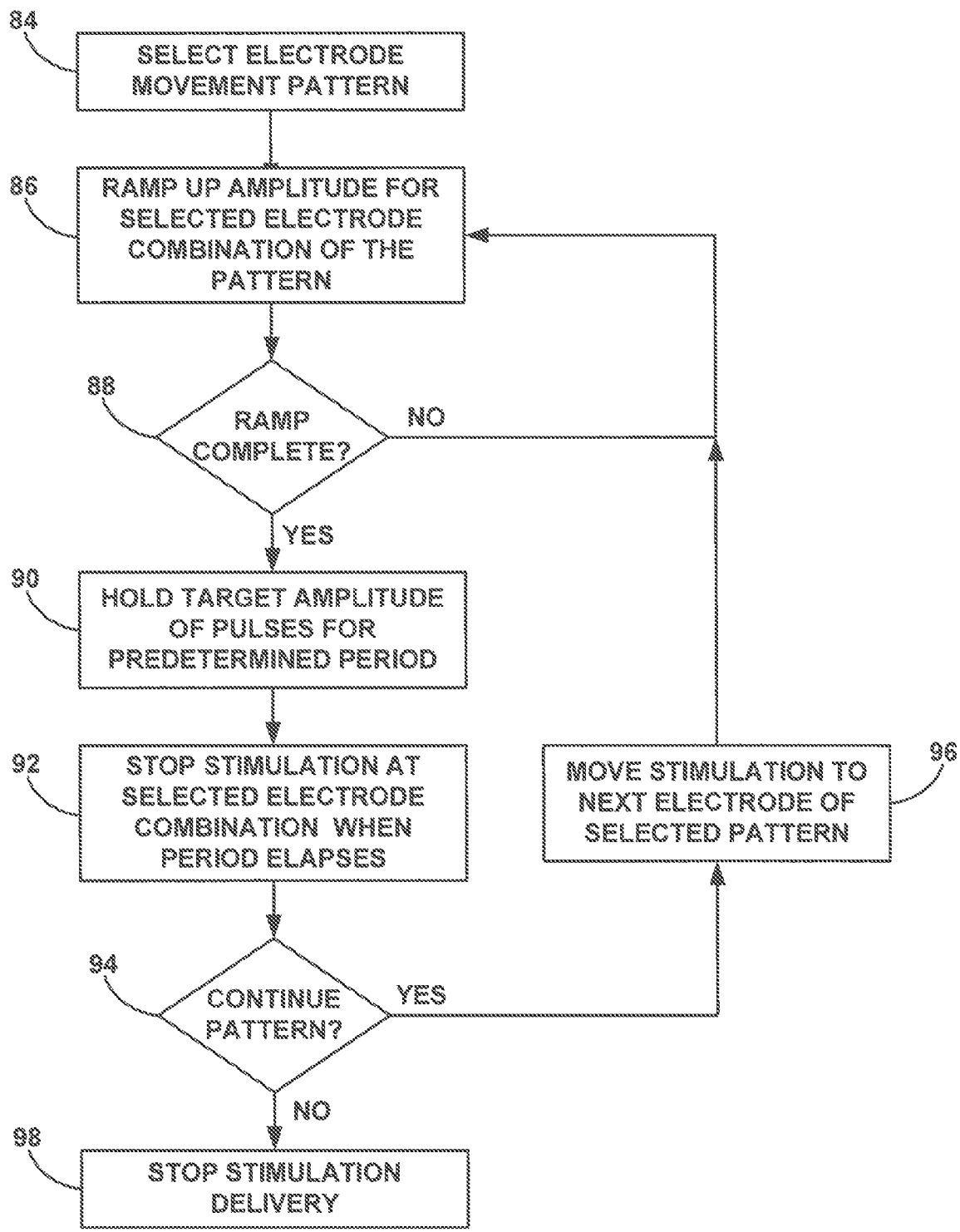
FIG. 6 is a flow diagram that illustrates an example process for moving electrical stimulation according to a spatial electrode movement pattern.

FIG. 6 is a flow diagram that illustrates an example process tier moving electrical stimulation according to a spatial electrode movement pattern (e.g., spatial electrode movement pattern 82 of FIG. 5). Although processor 30 of IMD 14 will be described as generally performing the technique of FIG. 6, the technique of FIG. 6 may instead be performed by a combination of processors 30 and 50 of programmer 20, or only processor 50, in other examples.

Processor 30 may select a spatial electrode movement pattern associated with the requested stimulation (84). Patient 12 may input the requested stimulation therapy to programmer 20 or processor 30 may retrieve the appropriate stimulation therapy based on detected conditions of patient 12 (e.g., posture or physiological conditions) or a specific time of day, for example. Processor 30 may also retrieve the appropriate set of stimulation parameters for the therapy.

Processor 30 may identify the first electrode combination of the spatial electrode movement pattern and ramp up the amplitude to the first electrode combination (86). The ramp up of stimulation may be iterative increases in the amplitude of subsequent pulses, for example. If the ramp is not complete ("NO" branch of block 88), processor 30 may continue to ramp up the amplitude to the target amplitude of the stimulation (86). If the ramp is finished and the amplitude has reached the target amplitude of the stimulation ("YES" branch of block 88), processor 30 may hold the target amplitude of pulses for the predetermined period of the electrode combination within the spatial electrode movement pattern (90).

When the period elapses (e.g., the progression rate indicates that stimulation is to move to the next electrode combination in the sequence), processor 30 may stop stimulation at the selected electrode combination (92). Processor 30 may then determine whether stimulation is to be continued according to the spatial electrode movement pattern (94). For example, processor 30 may check for any received input or other command that may indicate a change in stimulation therapy. If processor 30 is to continue stimulation according to the spatial electrode movement pattern ("YES" branch of block 94), processor 30 may move stimulation by selecting the next electrode combination of the selected spatial electrode movement pattern (96). In this manner, processor 30 may control therapy module 34 to repeat stimulation using the spatial electrode movement pattern. Processor 30 may then ramp up the amplitude for the new electrode combination of the spatial electrode movement pattern (86). If processor 30 is to stop delivering electrical stimulation ("NO" branch of block 94), processor 30 may stop delivering stimulation to patient 12 (98).

The process or FIG. 6 may be continued for any selected spatial electrode movement pattern. If a new spatial electrode movement pattern is selected, the process may begin again. In other examples, a ramp may not be used when first delivering stimulation after changing the electrode combination. The electrical stimulation delivered by each electrode combination may be a burst of pulses, multiple bursts of pulses, a continuous waveform, or any other type of electrical stimulation. Although the set of stimulation parameters may be unchanged throughout the spatial electrode movement pattern, one or more stimulation parameters (e.g., amplitude, pulse width, or pulse frequency) may be varied between electrode combinations of the spatial electrode movement pattern. This variation may account for different tissues, nerves, or sensitivities at different locations within patient 12.

For example, different stimulation parameters such as amplitude may be calibrated or set for each electrode or electrode combination. This calibration may set the amplitudes for each of the perception threshold, motor threshold, and therapeutic threshold. Alternatively, or additionally, the calibration may set high intensity stimulation levels such that patient 12 may toggle between different levels of stimulation during use. Table 1 provides an example calibration for eight electrodes used in a spatial electrode movement pattern. Each of the thresholds or levels of Table 1 may be determined experimentally, extrapolated, or modeled based on tissue models and electrical field models.

TABLE 1

| Electrode | Perception Threshold (V) | Strong & Comfortable (V) | Strong & Intense (V) | Uncomfortable (V) |
|---|---|---|---|---|
| 0 | 2.0 | 3.0 | 3.6 | 3.7 |
| 1 | 2.5 | 4.0 | 4.1 | 4.2 |
| 2 | 1.0 | 3.0 | 3.5 | 4.0 |
| 3 | 2.0 | 3.5 | 4.0 | 4.2 |
| 4 | 1.5 | 4.0 | 4.1 | 5.0 |
| 5 | 2.0 | 4.0 | 4.2 | 5.0 |
| 6 | 1.0 | 3.5 | 4.0 | 4.5 |
| 7 | 1.5 | 4.5 | 4.6 | 5.0 |

As shown in Table 1, the voltage (V) amplitudes for each threshold is provided for each electrode. The amplitude of the perception threshold may generally indicate the amplitude or intensity at which patient 12 can feel any effect from stimulation. The strong and comfortable threshold may be the intensity at which patient 12 feels paresthesia at an acceptable level. The strong and intense threshold may be the intensity at which patient 12 feels paresthesia but the feelings are very pronounced while not being uncomfortable or painful. The uncomfortable threshold may be the intensity at which patient 12 can no longer endure stimulation. Stimulation at or above the uncomfortable threshold may be avoided for use with patient 12. Data of Table 1 may be stored in memory 32 of IMD 14 and/or memory 52 of programmer 20. In some examples, Table 1 may also include motor thresholds and therapeutic thresholds. Each of the spatial electrode movement patterns described herein may be delivered with intensities defined as strong and comfortable, strong and intense, or at any other intensity or amplitude level requested by patient 12 or the clinician.

In some examples, bipolar electrode combinations may provide more intense or more localized stimulation therapy than unipolar electrode combinations at the same amplitudes. Therapies intended to provide feelings of pressure, strong sensations, or even almost uncomfortable intensities may be delivered using bipolar electrode combinations. These higher intensity stimulations may be delivered with bursts of pulses within each step of the sequence of the spatial electrode movement pattern. For example, the bursts of pulses may be delivered at a rate between approximately 2 and 4 Hz while the progression rate may be approximately 1 Hz. The pulses within each burst may be delivered with a pulse frequency between 10 Hz and 500 Hz, for example. Burst rates may be between approximately 1 Hz and 20 Hz, or at any rate faster than the progression rate of the stimulation movement.

Table 1 illustrates that the stimulation parameters may be different for each electrode or electrode combination in the spatial electrode movement pattern. If patient 12 requests any changes to the intensity or amplitude during therapy, programmer 20 and/or IMD 14 may make a global change based on the relative amplitudes stored in Table 1. For example, patient 12 may toggle between the strong and comfortable level and the strong and intense level. In another example, patient 12 may request a 0.2 V increase in amplitude when stimulation is delivered with electrode 2. Programmer 20 and/or IMD 14 may apply the increase to all other electrodes as an absolute magnitude change to other amplitudes or a percentage change to the other amplitudes.

Figure 7:
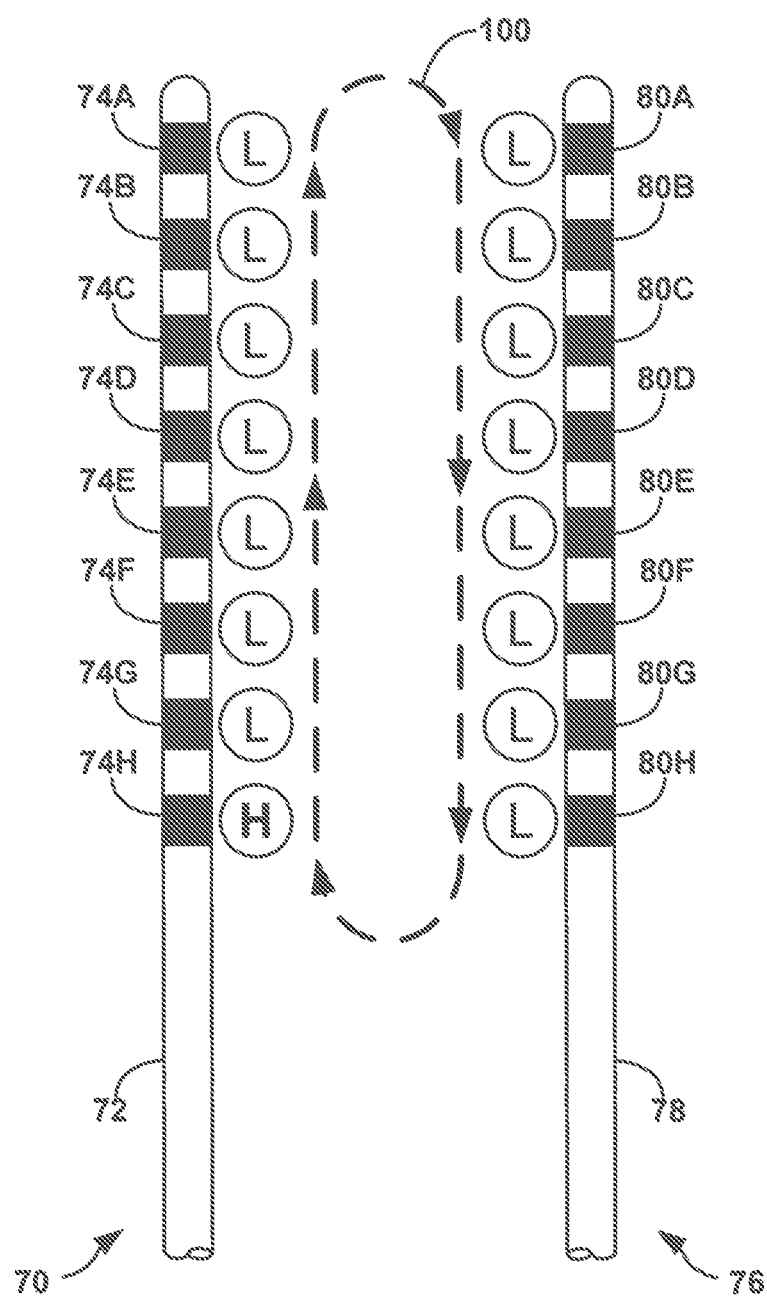
FIG. 7 is a conceptual diagram illustrating an example circular spatial electrode movement pattern for moving high intensity electrical stimulation within a low intensity background electrical stimulation.

FIG. 7 is a conceptual diagram illustrating example circular spatial electrode movement pattern 100 for moving high intensity electrical stimulation within a low intensity background electrical stimulation. Spatial electrode movement pattern 100 may be similar to spatial electrode movement pattern 82 of FIG. 5; however, background stimulation may be provided to patient 12 in FIG. 7. When electrode stimulation is selected to be delivered by electrodes 74 and 80, spatial electrode movement pattern 100 may be selected to define the sequence with which active electrodes are moved between electrodes 74 and 80. When all electrodes 74 and 80 are used to provide some type of stimulation, spatial electrode movement pattern 100 may essentially define how stimulation parameters change for each electrode combination over time.

IMD 14 may deliver a high intensity stimulation "H" and a low intensity stimulation "L". The low intensity stimulation may be referred to as background stimulation. Even though the low intensity stimulation may be set to a level exceeding the perception threshold or therapeutic threshold. For example, the low intensity stimulation may be relatively less identifiable to patient 12 than the high intensity stimulation. For example, the high intensity stimulation may be set to an intensity above a motor threshold to provide massaging stimulation therapy. Alternatively, the high intensity stimulation may provide more efficacious pain management than the low intensity stimulation. The low intensity stimulation may also be defined a set of parameters that includes at least one of lower amplitude, lower pulse rate, and shorter pulse width than the set of parameters that defines the high intensity stimulation.

IMD 14 may start delivering electrical stimulation with high intensity at electrode 74H (at least part of an electrode combination with one or more other electrodes on the housing of IMD 14 or one or more of electrodes 74 and 80) as indicated by the "H" icon. When the progression rate indicates that stimulation is to be moved, IMD 14 may change stimulation parameters for at least two of electrodes 74 and 80. IMD 14 may change the high intensity stimulation at electrode 74H to low intensity stimulation. IMD 14 may also change the low intensity stimulation at electrode 74G to the high intensity stimulation according to spatial electrode movement pattern 100. In some examples, all of electrodes 74 and 80 deliver low intensity stimulation or high intensity stimulation. In other examples, only a subset of electrodes 74 and 80 may deliver electrical stimulation such that at least one of electrodes 74 and 80 is not an anode or cathode during each electrode configuration of spatial electrode movement pattern 100.

In some examples, IMD 14 may first change the parameters for electrode 74H and then change the parameters for electrode 74G such that only one electrode combination delivers high intensity stimulation at one time. In other examples, IMD 14 may first change the parameters for electrode 74G to the high intensity stimulation and then subsequently change the stimulation parameters for electrode 74H to the low intensity stimulation. In this order, multiple electrode combinations may deliver the high intensity stimulation at the same time. When changing stimulation parameters, IMD 14 may ramp up amplitude and/or ramp down amplitude. Alternatively, IMD 14 may simultaneously ramp up the intensity (e.g., amplitude) at electrode 74G and ramp down the intensity (e.g., amplitude) at electrode 74H. These techniques for changing the stimulation according to spatial electrode movement pattern 100 may be applied to each electrode combination of the sequence for spatial electrode movement pattern 100. Movement of the active electrode may continue in the direction of the arrows of spatial electrode movement pattern 100 (e.g., up lead 70 and then down lead 76) until instructions command the stimulation is changed or stopped or a user provides an input to terminate the stimulation. Spatial electrode movement pattern 100 may also repeat until stimulation is terminated.

In a unipolar stimulation configuration as shown in FIG. 7, each of electrodes 74A and 80A may be cathodes and the electrode carried by the housing of IMD 14 may be an anode. Although only one electrode is shown as delivering high intensity stimulation in FIG. 7, multiple electrodes may deliver high intensity stimulation in other examples. The multiple electrodes may be adjacent electrodes, electrodes separated by one or more electrodes, or even electrodes on both leads 70 and 76. In other examples, electrodes 74 and 80 may be used in a bipolar configuration and moved in the circular manner of spatial electrode movement pattern 100. For example, electrode 74H may be a cathode and all other electrodes may be anodes. In some examples, multiple electrodes may be cathodes and the remaining electrodes may be anodes. In other multipolar examples, the high intensity stimulation may be delivered by one set of cathodes and anodes and the low intensity stimulation may be delivered by another set of cathodes and anodes. Although all electrodes 74 and 80 may be used to deliver high and low intensity simulation, one or more electrodes may not deliver the low intensity stimulation in other examples.

Figure 8:
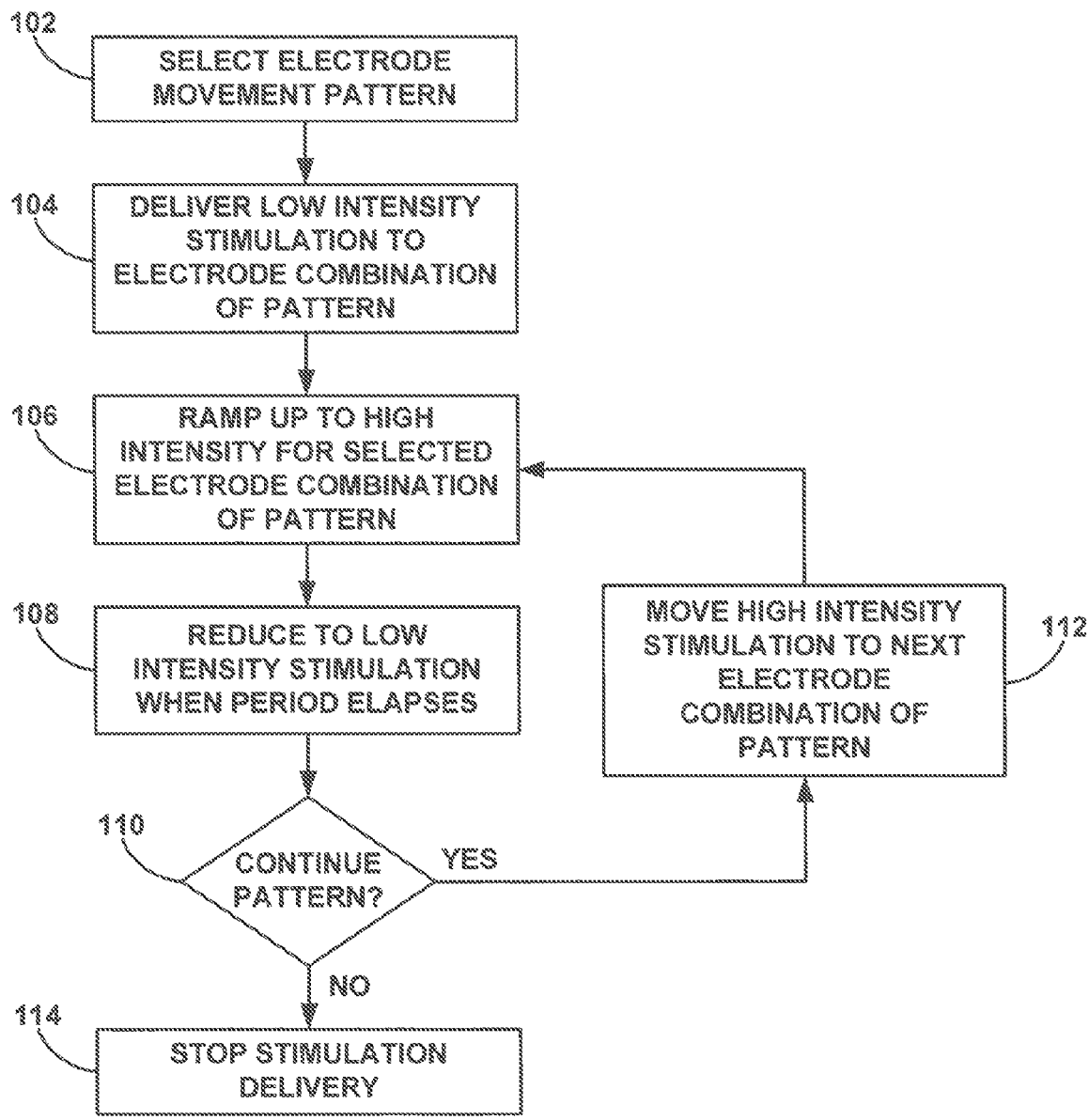
FIG. 8 is a flow diagram that illustrates an example process for moving high intensity electrical stimulation within a low intensity background electrical stimulation.

FIG. 8 is a flow diagram that illustrates an example process for moving high intensity electrical stimulation within a low intensity background electrical stimulation. The process of FIG. 8 may be similar to the process of FIG. 6; however, low intensity background electrical stimulation is also delivered in the process of FIG. 8. Although processor 30 of IMD 14 will be described as generally performing the technique of FIG. 8, the technique of FIG. 8 may instead be performed by a combination of processors 30 and 50 of programmer 20, or only processor 50, in other examples.

Processor 30 may select a spatial electrode movement pattern associated with the requested stimulation (102). Patient 12 may input the requested stimulation therapy to programmer 20 or processor 30 may retrieve the appropriate stimulation therapy based on detected conditions of patient 12 (e.g., posture or physiological conditions) or a specific time of day, for example. Processor 30 may also retrieve the appropriate set of stimulation parameters for the therapy, such as the stimulation parameters needed for both the high intensity stimulation and the low intensity stimulation.

Processor 30 may deliver the low intensity stimulation to selected electrode combinations of spatial electrode movement pattern 100 (104). Processor 30 may also identify the first electrode combination of the spatial electrode movement pattern for the high intensity stimulation and ramp up the amplitude to the high intensity for the first electrode combination (106). In the unipolar example, each electrode combination may include a reference electrode (e.g., an anode) along with one or more cathodes on leads 70 and/or 76. The reference electrode may be an electrode disposed on the housing of IMD 14, one of electrodes 74 or 80, or a different electrode implanted in patient 12 or disposed on the external surface of patient skin. Processor 30 may then hold the target amplitude of high intensity pulses for the predetermined period of the electrode combination within spatial electrode movement pattern 100.

When the progression rate indicates that the high intensity stimulation is to be moved to the next electrode combination of spatial electrode movement pattern 100, processor 30 may reduce the intensity of the first electrode combination to the low intensity (108). This reduction in intensity (e.g., amplitude, pulse rate, and/or pulse width) may be completed abruptly or according to a ramp. Processor 30 may then determine whether stimulation is to be continued according to spatial electrode movement pattern 100 (110). For example, processor 30 may check for any received input or other command that may indicate a change in stimulation therapy. If processor 30 is to continue stimulation according to the spatial electrode movement pattern ("YES" branch of block 110), processor 30 may move the high intensity stimulation by selecting the next electrode combination of the selected spatial electrode movement pattern 100 (112). Processor 30 may then ramp up the stimulation for the new electrode combination of the spatial electrode movement pattern (106). If processor 30 is to stop delivering electrical stimulation ("NO" branch of block 110), processor 30 may stop delivering stimulation to patient 12 (114).

The process of FIG. 8 may be continued for any selected spatial electrode movement pattern. If a new spatial electrode movement pattern is selected, the process may begin again. In other examples, a ramp may not be used when changing stimulation parameters when starting or moving electrical stimulation. The electrical stimulation delivered by each electrode combination may be a burst of pulses, multiple bursts of pulses, a continuous waveform, or any other type of electrical stimulation. Although the set of stimulation parameters for the high or low intensity stimulation may be unchanged throughout the spatial electrode movement pattern, one or more stimulation parameters (e.g., amplitude, pulse width, or pulse frequency) may be varied between electrode combinations of the spatial electrode movement pattern. This variation may account for different tissues, nerves, or sensitivities at different locations within patient 12.

Figure 9:
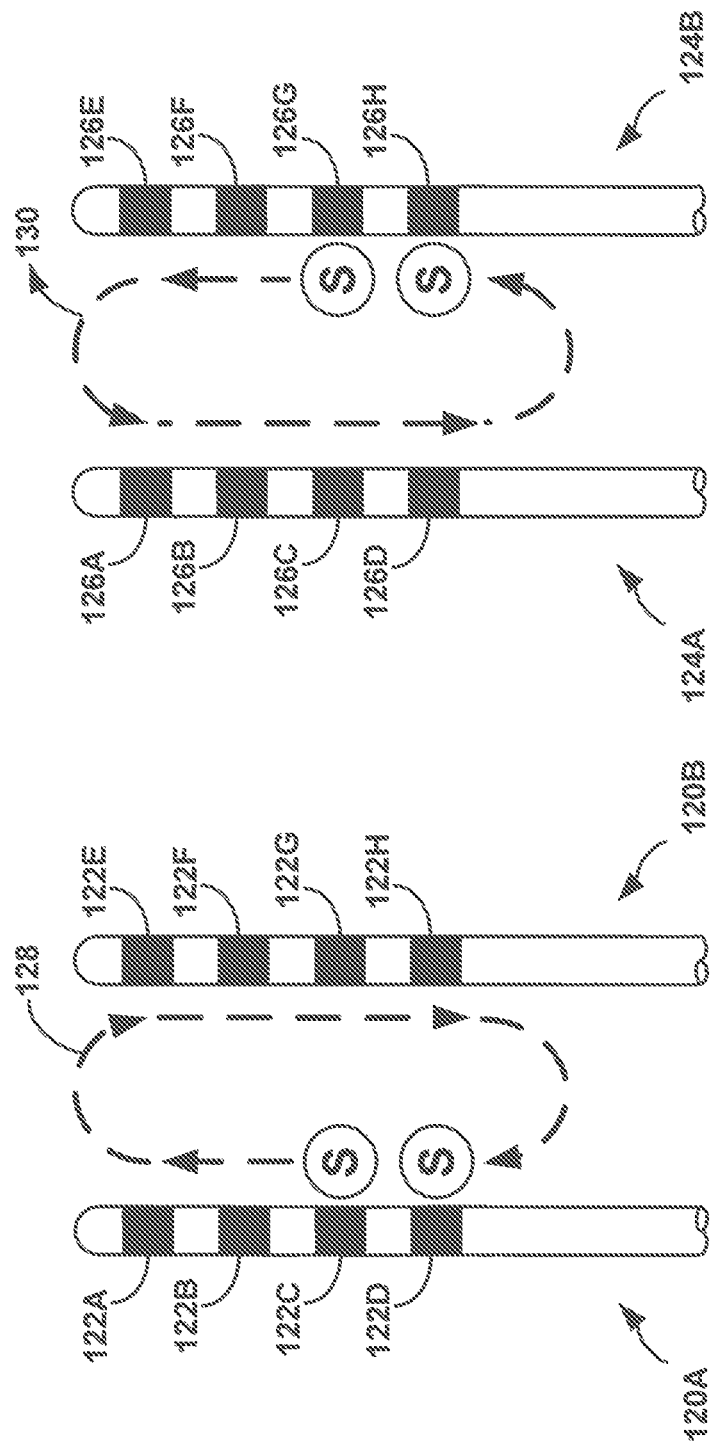
FIG. 9 is a conceptual diagram illustrating example dual circular spatial electrode movement patterns for moving electrical stimulation between a plurality of electrodes.

FIG. 9 is a conceptual diagram illustrating example dual circular spatial electrode movement patterns 128 and 130 for moving electrical stimulation between a plurality of electrodes. As shown in FIG. 9, leads 120A, 120B, 124A, and 124B may be configured to be implanted within patient 12 and coupled to PAD 14. Leads 120A, 120B, 124A, and 124B may be similar to leads 16, 18A, 18B, 70 and 78. Lead 120A may carry four electrodes 122A, 122B, 122C, and 122D (collectively "electrodes 122"). Lead 120B may carry four electrodes 122E, 122F, 122G, and 122H (collectively "electrodes 122"). Lead 124A may carry four electrodes 126A, 126B, 126C, and 126D (collectively "electrodes 126"). Lead 124B may carry four electrodes 126E, 126F, 126G, and 126H (collectively "electrodes 126").

Spatial electrode movement patterns 128 and 130 may be similar to spatial electrode movement pattern 82 of FIG. 5; however, movement patterns 128 and 130 may define two different concurrent stimulation movements for patient 12 in FIG. 9. Spatial electrode movement patterns 128 and 130 may separately provide different moving stimulation fields. The electrical stimulation from patterns 128 and 130 may be defined by similar stimulation parameters or different stimulation parameters. Stimulation from patterns 128 and 130 may be delivered to different areas of patient 12. These different areas may be bilateral areas in some examples. Generally, stimulation from patterns 128 and 130 may be delivered at the same time (e.g., simultaneously). In other examples, one or more pulses from patterns 128 and 130 may alternate with each other on an equal duty cycle or a duty cycle biased to one of patterns 128 and 130.

As shown in the example of FIG. 9, and for each of spatial electrode movement patterns 128 and 130, multiple electrodes may be used for each of the unipolar electrode combinations of the sequence in the respective patterns. A reference electrode on the housing of IMD 14, for example, may be used as a part of each electrode combination. In other examples, a single electrode (e.g., a cathode) may be used for each step of the sequence. Alternatively, bipolar electrode combinations may be used for spatial electrode movement patterns 128 and 130. In other words, each of the electrode combinations of each step in the sequence of patterns 128 and 130 may include an anode and a cathode. For example, electrodes 122C and 126G may be cathodes while electrodes 122D and 126H may be anodes.

Spatial electrode movement patterns 128 and 130 may move stimulation in opposite circular patterns. For example, IMD 14 may start delivering electrical stimulation at electrodes 122D and 122C (at least part of an electrode combination) as indicated by the "S" icons next to each electrode. Similarly, IMD 14 may start delivering electrical stimulation at electrodes 126H and 126G as indicated by the "S" icons next to each electrode. As described above, electrode pair 126H and 126G and electrode pair 122D and 122C may all be cathodes with a reference electrode (e.g., an anode) located at the housing of IMD 14. In a bipolar or multipolar configuration, each electrode pair may include an anode and a cathode. When the progression rate indicates that stimulation is to be moved, IMD 14 may terminate stimulation with electrodes 122D, 122C, 126H, and 126G and then subsequently begin stimulation with electrodes 122B, 122A, 126F, and 126E, respectively according to the sequences of spatial electrode movement patterns 128 and 130.

Movement of the active electrodes may continue in the direction of the arrows of spatial electrode movement patterns 128 and 130 until instructions command the stimulation is changed or stopped or a user provides an input to terminate the stimulation. Both of spatial electrode movement patterns 128 and 130 may also repeat until stimulation is terminated. In other examples, spatial electrode movement patterns 128 and 130 may not move the entire electrode combination be each step in the sequence. Instead, the pair of electrodes used to deliver electrical stimulation may move over to only one electrode. For example, electrode 126H may be removed from the electrode combination and electrode 126F may be added to the electrode combination when moving to the next step in the sequence.

Although two electrodes are shown in be used for each step of the sequence in spatial electrode movement patterns 128 and 130, only one or more than two electrodes may be used in other examples. Multiple electrodes for each spatial electrode movement pattern may be adjacent electrodes, electrodes separated by one or more electrodes, or even electrode combinations spanning multiple leads. In this manner, two or more electrodes that may or may not be adjacent to each other may be moved in a specific spatial electrode movement pattern. Although it may be beneficial for each spatial electrode movement pattern to be similar or symmetrical, other combinations of spatial electrode movement patterns may have differing number of electrodes for each step in a sequence, utilize a different number of steps in the sequence, or even move with different progression rates.

Spatial electrode movement patterns 128 and 130 are shown moving electrical stimulation in opposing circles (e.g., pattern 128 moves clockwise and pattern 130 moves counter-clockwise). In other examples, these movements may be switched between the two patterns or each pattern may move or rotate in the same direction. In some examples, three or more different spatial electrode movement patterns may be simultaneously used to move electrical stimulation among the electrodes.

Alternative examples may not include circular waves or movement of electrodes. Instead, a linear wave, for example, of electrode movement may be defined that moves across the array of electrodes 122 and 126. For example, a spatial electrode movement pattern may define a vertical wave of movement that moves down each electrode of each respective lead. In other words, stimulation may move from electrodes 122A, 122E, 126A, and 126E towards electrodes 122D, 122H, 126D, and 126H. Once stimulation has traversed each lead, the active electrodes may repeatedly move down the leads again or reverse position back up each lead. In this manner, electrical stimulation may be moved proximally or distally along each lead in a wave-like pattern. Similarly, a horizontal wave of electrical stimulation may move across each lead such that multiple or all electrodes of one lead transitions into electrodes from the adjacent lead. For example, electrodes 122A, 122B, 122C, and 122D may be changed from one step of the sequence to electrodes 122E, 122F, 122G, and 122H in the next step of the sequence. Diagonal waves of movement may also be provided in other examples.

Each time that electrical stimulation is moved to a new electrode combination (e.g., electrodes 122C and 122D to electrodes 122A and 122B), IMD 14 may ramp up the amplitude of the electrical stimulation. This ramp up of amplitude may be performed to reduce abrupt sensations to patient 12. This ramp up of amplitude or another stimulation parameter may be completed within 10 seconds, for example. In some examples, the ramp may be completed within one or more pulses of the burst provided by the electrode combination. Simulation may begin at any staring position within the respective spatial electrode movement patterns 128 and 130, at the location last used for electrical stimulation, or at a position selected by a clinician or patient 12.

Leads 120A, 120B, 124A, and 124B may include an equal number of electrodes. In other examples, leads 120A, 120B, 124A, and 124B may include unequal numbers of electrodes. Movement of electrical stimulation may be performed using all of the electrodes of implanted leads 120A, 120B, 124A, and 124B, for example. However, fewer than all of the electrodes may be utilized for a spatial electrode movement pattern in other examples. Generally, four or more electrodes may be utilized when moving electrical stimulation. For example, eight electrodes, sixteen electrodes, or even thirty two or more electrodes may be utilized. In some examples, the clinician or patient 12 may blacklist or remove one or more electrodes from a spatial electrode movement pattern if that electrode provides an uncomfortable or otherwise undesirable sensation to patient 12.

Figure 10:
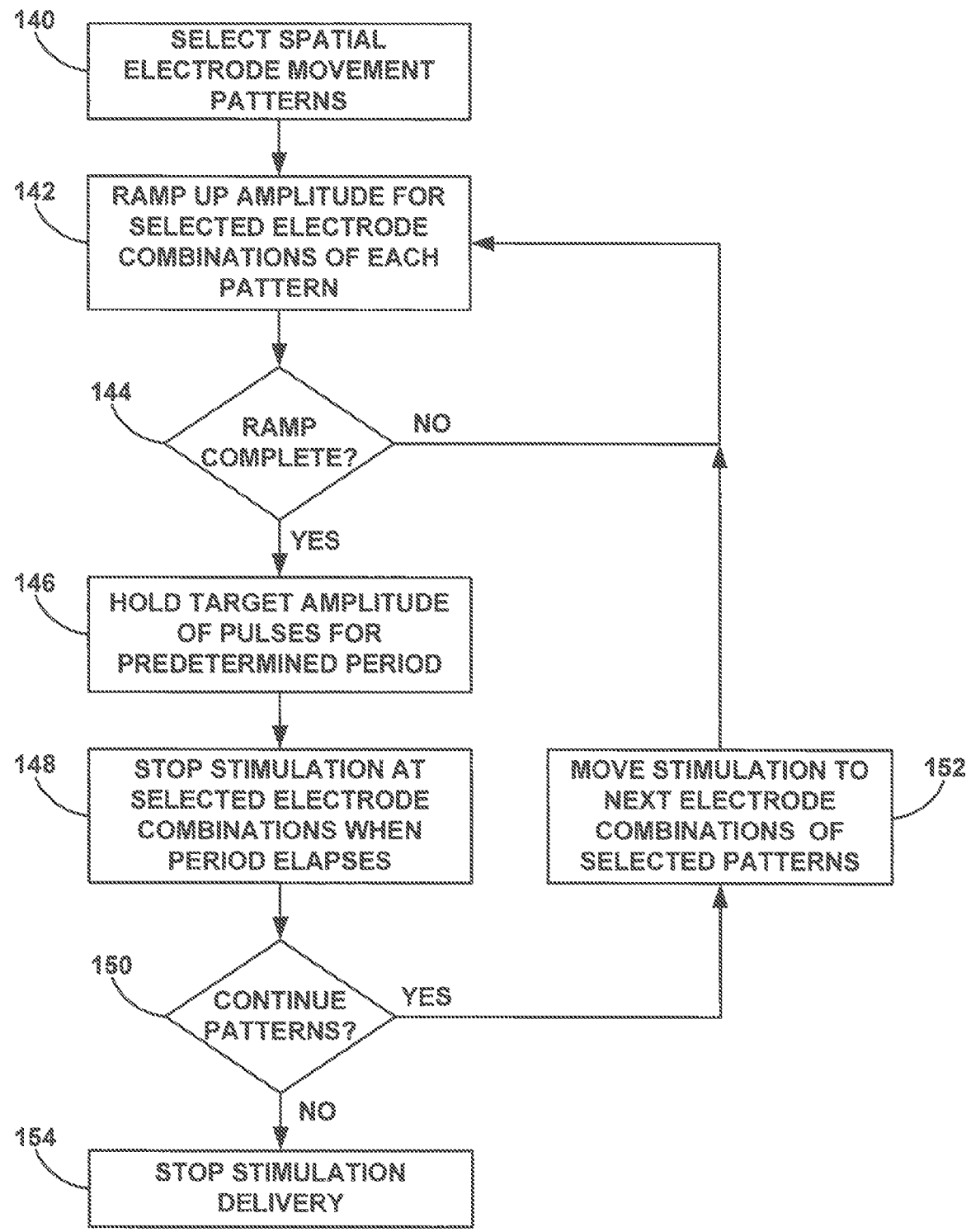
FIG. 10 is a flow diagram that illustrates an example process for moving electrical stimulation according to dual spatial electrode movement patterns.

FIG. 10 is a flow diagram that illustrates an example process for moving electrical stimulation according to dual spatial electrode movement patterns 128 and 130 of FIG. 9. The process of FIG. 10 may be similar to the process of FIG. 6; however, FIG. 10 describes two concurrently used spatial electrode movement patterns. Although processor 30 of IMD 14 will be described as generally performing the technique of FIG. 10, the technique of FIG. 10 may instead be performed by a combination of processors 30 and 50 of programmer 20, or only processor 50, in other examples.

Processor 30 may select the spatial electrode movement patterns associated with the requested stimulation (140). Patient 12 may input the requested stimulation therapy to programmer 20 or processor 30 may retrieve the appropriate stimulation therapy based on detected conditions of patient 12 (e.g., posture or physiological conditions) or a specific time of day, for example. Processor 30 may also retrieve the appropriate set of stimulation parameters for the therapy.

Processor 30 may identify the first electrode combinations of the spatial electrode movement pattern and ramp up the amplitude for each of the electrode combinations of the respective spatial electrode movement patterns (142). The ramp up of stimulation may be iterative increases in the amplitude of subsequent pulses, for example. If the ramp is not complete ("NO" branch of block 144), processor 30 may continue to ramp up the amplitude for each electrode combination to the target amplitude of the stimulation (142). If the ramp is finished and the amplitude has reached the target amplitude of the stimulation ("YES" branch of block 144), processor 30 may hold the target amplitude of pulses tier each electrode combination for the predetermined period within the spatial electrode movement pattern (146).

When the period elapses (e.g., the progression rate indicates that stimulation is to move to the next electrode combination in the respective sequences of patterns 128 and 130), processor 30 may stop stimulation at the selected electrodes of the electrode combinations (148). Processor 30 may then determine whether stimulation is to be continued according to the spatial electrode movement patterns (150). For example, processor 30 may check for any received input or other command that may indicate a change in stimulation therapy. If processor 30 is to continue stimulation according to the spatial electrode movement patterns ("YES" branch of block 150), processor 30 may move stimulation by selecting the next electrode combinations of the respective selected spatial electrode movement patterns (152). Processor 30 may then ramp up the amplitude for the new electrode combinations of the respective spatial electrode movement patterns (142). If processor 30 is to stop delivering electrical stimulation ("NO" branch of block 150), processor 30 may stop delivering stimulation to patient 12 (154).

The process of FIG. 10 may be expanded to handle concurrent spatial electrode movement patterns with different progression rates, numbers of electrode combinations with each pattern, or other differences that require separate instructions for each spatial electrode movement pattern. For example, processor 30 may separate control the stimulation for each of the multiple spatial electrode movement patterns. Although a single therapy module 34 may be configured to deliver electrical stimulation according to two spatial electrode movement patterns, multiple therapy modules and/or current or voltage sources may be utilized in other examples.

Figure 11:
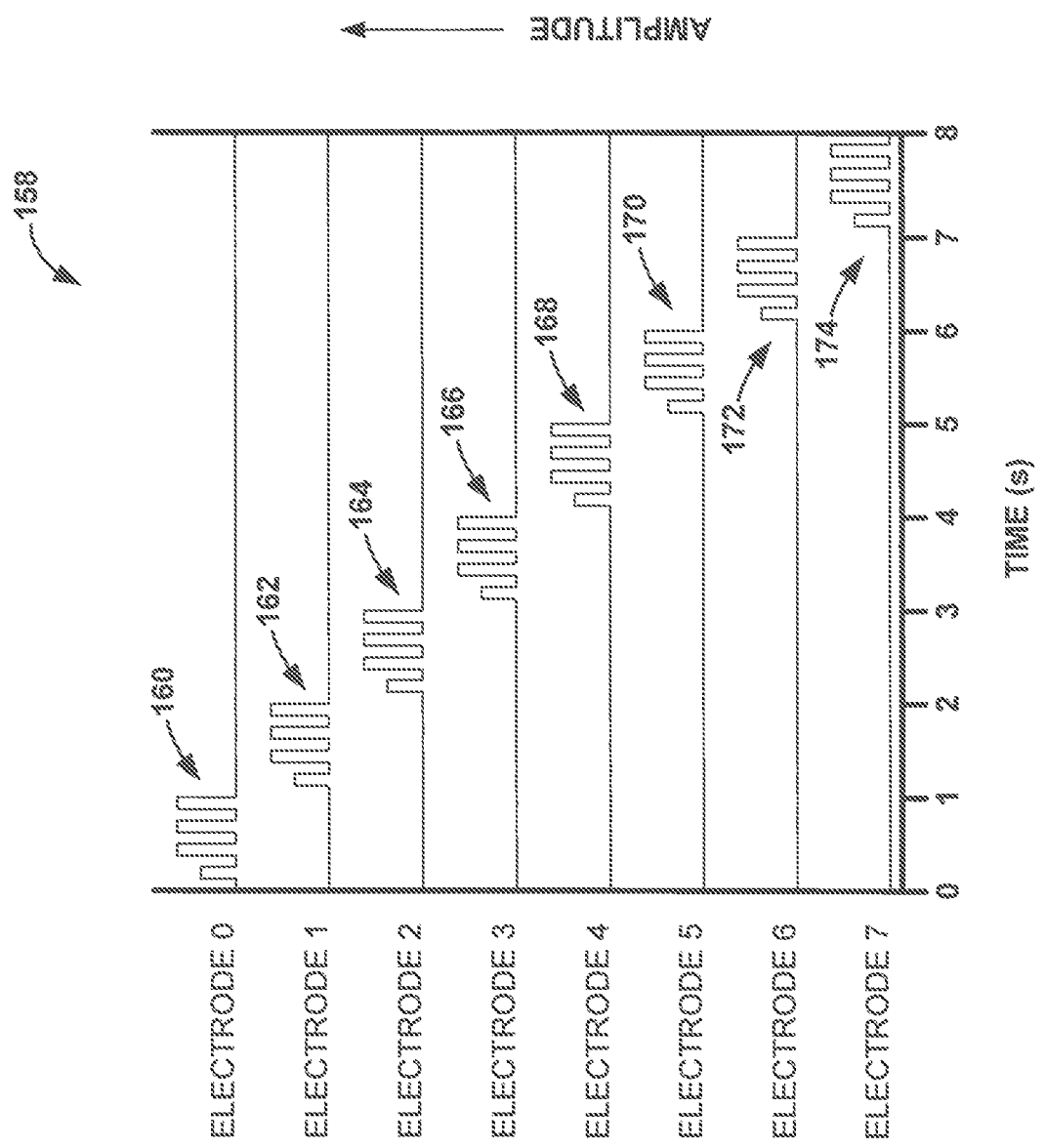
FIG. 11 is an example timing diagram for moving electrical stimulation according to a spatial electrode movement pattern.

FIG. 11 is an example timing diagram 158 for moving electrical stimulation according to a spatial electrode movement pattern. As shown in the example of FIG. 11, timing diagram 158 may illustrate the change in electrical stimulation according to a single spatial electrode movement pattern (e.g., spatial electrode movement pattern 82 of FIG. 5). Timing diagram 158 shows the amplitude of each electrode used in the spatial electrode movement pattern at any given time, and the relative amplitude for each of the electrodes. In addition, time progresses toward the right. For example, stimulation may begin at the zero time mark and the sequence of the spatial electrode movement pattern may finish at the eight second mark.

Electrical stimulation may begin with burst 160 delivered with electrode 0. In the example of FIG. 11, for purposes of illustration, electrodes 0 through 7 may form unipolar electrode combinations with a housing electrode of IMD 14. Although the change in burst of pulses from different electrodes may be similar for bipolar or multipolar electrode combinations, the timing diagrams for bipolar or multipolar electrode combinations would refer to each electrode that contributes to the pulses. Burst 160 may contain a plurality of pulses that are delivered to patient 12. The first pulses may have an increasing amplitude during the ramp before reaching the target amplitude of the remaining pulses in burst 160. Although only four pulses are shown in the approximately one second duration of burst 160, fewer than four pulses or many more than four pulses may be delivered during burst 160. The number of pulses in burst 160, and the other bursts of timing diagram 158, are provided for illustration.

The progression rate of timing diagram 158 may define that electrode combinations of the spatial electrode movement pattern are to be changed at a rate of approximately 1 Hz. In other words, each burst will last a duration of approximately 1 second. Other progression rates as described herein may be used in other examples. Once the progression rate indicates that electrical stimulation is to be moved, IMD 14 may change to the next electrode combination (e.g., electrode 1) and deliver the next pulses in burst 162. Burst 162 may also provide a ramp up in amplitude for the pulses. The spatial electrode movement pattern continues to define the change in electrode combinations over time such that bursts 164, 166, 168, 170, 172, and 174 are provided to patient 12 from electrodes 2 through 7, respectively. Once the pulses of burst 174 are delivered, IMD 14 may repeat the spatial electrode movement pattern by again delivering pulses from electrode 0 similar to burst 160. This process may continue until IMD 14 is instructed to change or terminate the stimulation.

Timing diagram 158 is provided as an example of one spatial electrode movement pattern that may be used to deliver moving electrical stimulation therapy. Timing diagrams for different spatial electrode movement patterns may include different number of pulses, a different sequence of changes between electrode combinations, a random movement or non-adjacent movement of electrode combinations within the sequence, or other variations. In some examples, pulses may proceed continuously even when electrode combinations are changed according to the spatial electrode movement pattern. In other examples, pulses may be delayed or paused between electrode combination changes such that the gap between pulses may be longer between bursts than the gap between pulses within a single burst.

Figure 12:
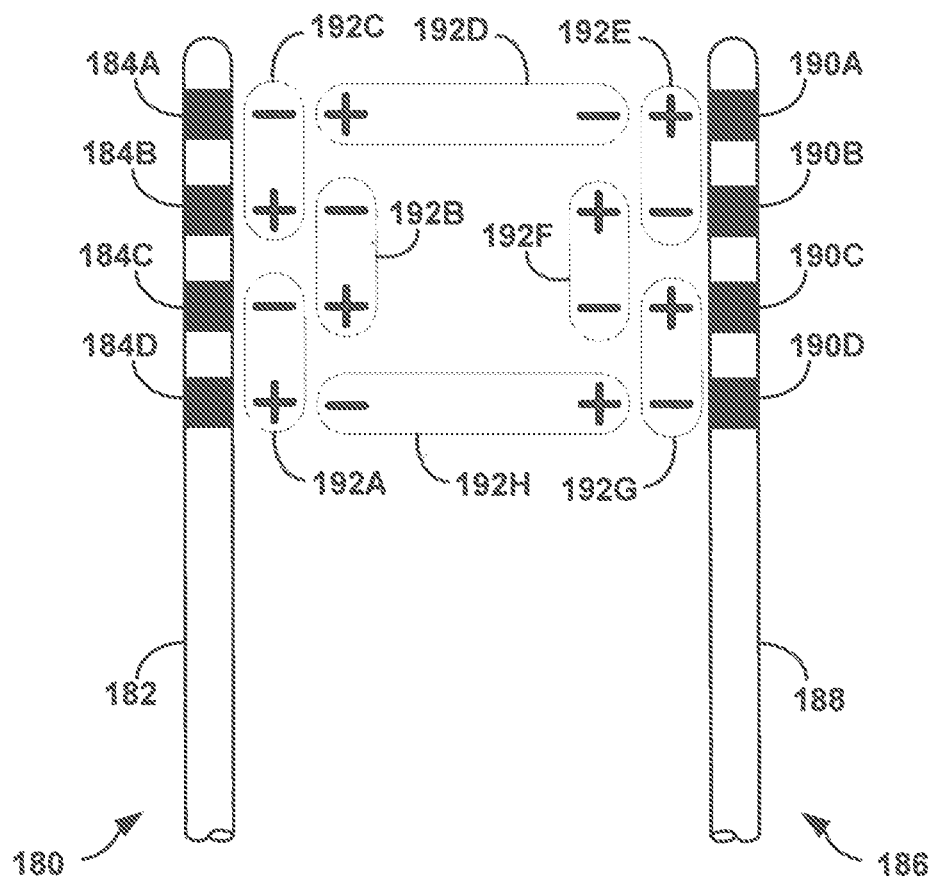
FIG. 12 is a conceptual diagram illustrating an example circular spatial electrode movement pattern for moving electrical stimulation between bipolar electrode combinations.

FIG. 12 is a conceptual diagram illustrating an example circular spatial electrode movement pattern for moving electrical stimulation between bipolar electrode combinations. The movement of stimulation in FIG. 12 may be similar to that of FIG. 5; however, FIG. 12 describes the movement of anodes and cathodes for bipolar electrode combinations according to the spatial electrode movement pattern. As shown in FIG. 12, leads 180 and 186 may be configured to be implanted within patient 12 and coupled to IMD 14. Leads 180 and 186 may be similar to leads 16, 18A, and/or 18B. Lead 180 may include lead body 182 that carries four electrodes 184A, 184B, 184C, and 184 (collectively "electrodes 184"). Lead 186 may include lead body 188 that carries four electrodes 190A, 190B, 190C, and 190D (collectively "electrodes 190").

When electrode stimulation is selected to be delivered by electrodes 184 and 190, the spatial electrode movement pattern may be selected to define the sequence with which active electrodes are moved between electrodes 184 and 190. For example, the spatial electrode movement pattern may define a sequence of bipolar electrode combinations 192A, 192B, 192C, 192D, 192E, 192F, 192 G, and 192H (collectively "electrode combinations 192"). Each bipolar electrode combination may include an anode and a cathode. Each electrode combination 192 indicates a step in the spatial electrode movement pattern, in other words, each electrode combination 192 is representative of a step in moving a single electrode combination between electrodes 184 and 190 over time.

As shown in FIG. 12, stimulation may begin with the first electrode combination 192A. Electrode combination 192A may define electrode 184D as an anode and electrode 184C as a cathode. When stimulation is determined to be moved to the next step in the sequence of the spatial electrode movement pattern, stimulation may be delivered with electrode combination 192B. Electrode combination 192B may define electrode 184C as an anode and electrode 184B as a cathode. Electrode combinations 192 may this retain approximately the same shape between movements, although electrode combinations spanning two leads (e.g., electrode combinations 192D and 192H) may have slightly different shapes depending on the distance between leads 180 and 186. In this manner, electrode combinations 192 may iterative move stimulation in a clockwise direction one electrode at a time. Electrode combinations 192 may also retain the orientation of the anode and cathode as stimulation is moved.

Each time that electrical stimulation is moved to a new electrode combination (e.g., electrode combination 192A to electrode combination 192B), IMD 14 may ramp up the amplitude of the electrical stimulation. This ramp up of amplitude may be performed to reduce abrupt sensations to patient 12. This ramp up of amplitude or another stimulation parameter may be completed within 10 seconds, for example. In some examples, the ramp may be completed within one or more pulses of the burst provided by the electrode combination.

Although stimulation may be started at electrode combination 192A, stimulation may be started at any electrode combination 192 of the spatial electrode movement pattern. The spatial electrode movement pattern is provided in a clockwise direction around electrodes 184 and 190. In other examples, the spatial electrode movement pattern may move in a counterclockwise direction. The direction of the spatial electrode movement pattern may be selected by the clinician, selected by patient 12, or alternated between repetitions of the spatial electrode movement pattern or instances that therapy is delivered using the spatial electrode movement pattern. The spatial electrode movement pattern may generally be described as a circular or rectangular pattern. In other examples, the spatial electrode movement pattern may represent patterns of other forms or shapes. For examples, the spatial electrode movement pattern may define a sequence of electrode combinations that move back and forth between leads 180 and 186. In addition, alternative spatial electrode movement patterns may include random sequences for moving the electrical stimulation.

In other examples, the spatial electrode movement pattern may move bipolar electrode combinations in a different fashion. For example, stimulation may be moved to the next electrodes that previously were not used to deliver stimulation. Stimulation may be moved from electrode combination 192A directly to electrode combination 192C, for example. In another example, the spatial electrode movement pattern may define movement of stimulation with alternating bipolar electrode combinations in each step. For example, when electrode combination 192A is changed to electrode combination 192B, electrode combination 192B may flip the anode and cathode such that electrode 184C would remain a cathode and electrode 184B would be an anode. In this manner, the electrical field shape may change between consecutive electrode combinations.

Although the spatial electrode movement pattern of FIG. 12 is described with regard to bipolar electrode combinations 192, multipolar electrode combinations may be used in other examples. The anodes and cathodes of each consecutive multipolar electrode combination may be rotated, flipped, or otherwise changed to slowly or quickly move the stimulation amongst electrodes 184 and 188, or some subset of electrodes thereof.

Leads 180 and 186 may include an equal number of electrodes. In other examples, leads 180 and 186 may include unequal numbers of electrodes. In some examples, more than two leads may be used or only one lead may be used. In the example of a single lead (e.g., only lead 180), the spatial electrode movement pattern may define traversal of all electrodes 184 from one end of lead 180 to the opposite end of lead 180 and back again. Alternatively, the spatial electrode movement pattern may only move in one direction such that the electrode movement pattern restarts at one end of lead 180 when the sequence finishes at the opposite end of lead 180.

Movement of electrical stimulation may be performed using all of the electrodes of implanted leads 180 and 186, for example. However, fewer than all of the electrodes may be utilized for a spatial electrode movement pattern in other examples. Generally, four or more electrodes may be utilized when moving electrical stimulation. For example, eight electrodes, sixteen electrodes, or even thirty two or more electrodes may be utilized. However, fewer than four electrodes may be used in some examples. In other examples, the clinician or patient 12 may blacklist or remove one or more electrodes from a spatial electrode movement pattern if that electrode provides an uncomfortable or otherwise undesirable sensation to patient 12.

According to the techniques and devices described herein, electrical stimulation may be moved to different anatomical regions of a patient according to a spatial electrode movement pattern. For example, a spatial electrode movement pattern may define a circular movement pattern that sequentially moves the active electrodes around one or more leads in a circular pattern. This electrical stimulation movement may be used to provide massaging therapy, acupuncture therapy, or migrating paresthesia for treating one or more symptoms of the patient. For example, the stimulation movement may be used to treat chronic back pain in a patient.

As described herein, a spatial electrode movement pattern may define a specific sequence of electrode combinations that result in movement of the electrical stimulation, and movement of therapy perceived by the patient, amongst a plurality of electrodes. In one example, the pattern may define a bipolar electrode combination that moves to different electrodes. In another example, the pattern may define bipolar electrode combinations in which an anode or a cathode remains at a fixed electrode and the corresponding anode or cathode moves between the electrodes. In another example, the pattern may define multipolar electrode combinations in which one or more cathodes and one or more anodes are grouped together and moved together between the electrodes. In an alternative example, the pattern may define multipolar electrode combinations in which an anode or cathode remains fixed on one electrode and the corresponding cathodes or anodes are moved together amongst the electrodes. In a further example, the pattern may define unipolar electrode combinations where an anode remains fixed at an electrode disposed on the housing of IMD 14 and one or more cathodes are moved together between the electrodes of the leads. In any of these examples, the spatial electrode movement pattern may define a sequence for changing electrode combinations such that the patient may perceive movement of stimulation therapy with respect to anatomical structures within the patient.

The disclosure also contemplates computer-readable storage media comprising instructions to cause a processor to perform any of the functions and techniques described herein. The computer-readable storage media may take the form of any volatile, non-volatile, magnetic, optical, or electrical media, such as a RAM, ROM, NVRAM, EEPROM, or flash memory, for example. The computer-readable storage media may be non-transitory. A programmer, such as patient programmer or clinician programmer, may also contain a more portable removable memory type to enable easy data transfer or offline data analysis.

The techniques described in this disclosure, including those attributed to IMD 14, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 30 of IMD 14, processor 50 of programmer 20, or any one or more parts of the techniques described herein may be implemented by a processor of one of IMD 14, programmer 20, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Various examples have been described. These and other examples are within the scope of the following claims.

What is claimed is:

1. A method for delivering electrical stimulation to a patient, the method comprising:
   receiving, by at least one processor, a spatial electrode movement pattern that defines a sequence with which first electrical stimulation is moved between a plurality of electrodes implanted within the patient;
   delivering the first electrical stimulation having a first stimulation intensity to the patient with electrodes of the plurality of electrodes selected according to the spatial electrode movement pattern for each step of the sequence, wherein the first electrical stimulation is moved, for each step of the sequence, between the plurality of electrodes according to the spatial electrode movement pattern;
   delivering, concurrently with the first electrical stimulation and during each step of the sequence, a second electrical stimulation having a second stimulation intensity to the patient with electrodes of the plurality of electrodes unselected by the spatial electrode movement pattern, the electrodes selected by the spatial electrode movement pattern and the electrodes unselected by the spatial electrode movement pattern comprising all of the plurality of electrodes, wherein the first stimulation intensity is greater than the second stimulation intensity; and
   repeating the spatial electrode movement pattern when delivering the first electrical stimulation and the second electrical stimulation to the patient.

2. The method of claim 1, wherein the spatial electrode movement pattern comprises a generally circular pattern among the plurality of electrodes.

3. The method of claim 1, wherein the spatial electrode movement pattern comprises a random pattern among the plurality of electrodes, and wherein each of the plurality of electrodes is used exactly once to deliver the first electrical stimulation during the random pattern.

4. The method of claim 1, wherein, for each respective step of the sequence: the electrodes of the plurality of electrodes selected according to the spatial electrode movement pattern comprise a first subset of the plurality of electrodes,
   the electrodes of the plurality of electrodes unselected by the spatial electrode movement pattern comprise a second subset of the plurality of electrodes different than the first subset, and
   the first subset and the second subset, combined, comprise all of the plurality of electrodes.

5. The method of claim 1, wherein delivering the first electrical stimulation comprises delivering the first electrical stimulation exceeding a perception threshold, and wherein the first electrical stimulation exceeding the perception threshold is configured to be perceived by the patient.

6. The method of claim 1, wherein:
delivering the first electrical stimulation comprises delivering the first electrical stimulation exceeding a motor threshold,
the first electrical stimulation exceeding the motor threshold is configured to cause muscle contractions in the patient, and
delivering the second electrical stimulation comprises delivering the second electrical stimulation exceeding a perception threshold of the patient and below the motor threshold of the patient.

7. The method of claim 1, wherein the plurality of electrodes are carried by one or more leads.

8. The method of claim 1, wherein:
delivering the first electrical stimulation comprises delivering the first electrical stimulation via a plurality of unipolar electrode combinations defined by the spatial electrode movement pattern; and
each of the plurality of unipolar electrode combinations comprises one of the plurality of electrodes and a housing electrode of an implantable medical device.

9. The method of claim 1, wherein:
delivering the first electrical stimulation comprises delivering the first electrical stimulation via a plurality of bipolar electrode combinations defined by the spatial electrode movement pattern; and
each of the plurality of bipolar electrode combinations comprise two of the plurality of electrodes.

10. The method of claim 1, wherein receiving the spatial electrode movement pattern comprises retrieving the spatial electrode movement pattern from a memory.

11. The method of claim 1, wherein the spatial electrode movement pattern defines movement of the first electrical stimulation between the plurality of electrodes at a rate of approximately 0.2 Hz and 2 Hz.

12. The method of claim 1, wherein the at least one processor is housed within one of an implantable medical device or an external programmer.

13. A system comprising:
a plurality of electrodes configured to be implanted within a patient;
at least one processor configured to receive a spatial electrode movement pattern that defines a sequence with which first electrical stimulation is moved between the plurality of electrodes; and
a therapy module configured to:
deliver the first electrical stimulation having a first stimulation intensity to the patient with electrodes of the plurality of electrodes selected according to the spatial electrode movement pattern for each step of the sequence; and
deliver, concurrently with the first electrical stimulation and during each step of the sequence, a second electrical stimulation having a second stimulation intensity to the patient with electrodes of the plurality of electrodes unselected by the spatial electrode movement pattern, the electrodes selected by the spatial electrode movement pattern and the electrodes unselected by the spatial electrode movement pattern comprising all of the plurality of electrodes, wherein the first stimulation intensity is greater than the second stimulation intensity, wherein the at least one processor is configured to:
control the therapy module to move the first electrical stimulation between each of the plurality of electrodes according to the spatial electrode movement pattern; and
control the therapy module to repeat the spatial electrode movement pattern when delivering the first electrical stimulation and the second electrical stimulation to the patient.

14. The system of claim 13, wherein the spatial electrode movement pattern comprises a generally circular pattern among the plurality of electrodes.

15. The system of claim 13, wherein the spatial electrode movement pattern comprises a random pattern among the plurality of electrodes, and wherein each of the plurality of electrodes is used exactly once to deliver the first electrical stimulation during the random pattern.

16. The system of claim 13, wherein, for each respective step of the sequence:
the electrodes of the plurality of electrodes selected according to the spatial electrode movement pattern comprise a first subset of the plurality of electrodes;
the electrodes of the plurality of electrodes unselected by the spatial electrode movement pattern comprise a second subset of the plurality of electrodes different than the first subset; and
the first subset and the second subset, combined, comprise all of the plurality of electrodes.

17. The system of claim 13, wherein:
the therapy module is configured to deliver the first electrical stimulation that exceeds at least one of a perception threshold and a motor threshold;
the first electrical stimulation that exceeds the perception threshold is configured to be perceived by the patient; and
the first electrical stimulation that exceeds the motor threshold is configured to cause muscle contractions in the patient.

18. The system of claim 13, further comprising one or more leads that carry the plurality of electrodes.

19. The system of claim 13, wherein the plurality of electrodes comprise at least eight electrodes.

20. The system of claim 13, further comprising an implantable medical device comprising a housing electrode, wherein:
the therapy module is configured to deliver the first electrical stimulation via a plurality of unipolar electrode combinations defined by the spatial electrode movement pattern; and
each of the plurality of unipolar electrode combinations comprises one of the plurality of electrodes and the housing electrode of the implantable medical device.

21. The system of claim 13, wherein:
the therapy module is configured to deliver the first electrical stimulation via a plurality of bipolar electrode combinations defined by the spatial electrode movement pattern; and
each of the plurality of bipolar electrode combinations comprise two of the plurality of electrodes.

22. The system of claim 13, further comprising a memory configured to store the spatial electrode movement pattern, wherein the at least one processor is configured to retrieve the spatial electrode movement pattern from the memory.

23. A computer-readable storage medium comprising instructions that cause at least one processor to:
receive a spatial electrode movement pattern that defines a sequence with which first electrical stimulation is moved between plurality of electrodes implanted within a patient;
deliver the first electrical stimulation having a first stimulation intensity to the patient with electrodes of the plurality of electrodes selected according to the spatial electrode movement pattern for each step of the sequence, wherein the first electrical stimulation is moved, for each step of the sequence, between each of the plurality of electrodes according to the spatial electrode movement pattern;

deliver, concurrently with the first electrical stimulation and during each step of the sequence, a second electrical stimulation having a second stimulation intensity to the patient with electrodes of the plurality of electrodes unselected by the spatial electrode movement pattern, the electrodes selected by the spatial electrode movement pattern and the electrodes unselected by the spatial electrode movement pattern comprising all of the plurality of electrodes, wherein the first stimulation intensity is greater than the second stimulation intensity; and repeat the spatial electrode movement pattern when delivering the first electrical stimulation and the second electrical stimulation to the patient.

* * * * *